US006589751B2

(12) United States Patent
Ferguson et al.

(10) Patent No.: US 6,589,751 B2
(45) Date of Patent: *Jul. 8, 2003

(54) IMMONOLOGICAL DETECTION OF THE HOMOCYSTAMIDE ADDUCT AND A THIOLACTONE IMMUNOASSAY FOR ENDOGENEOUS HOMOCYSTEINE

(75) Inventors: Eric Ferguson, Milwaukee, WI (US); Sampath Parthasarathy, Atlanta, GA (US); Balaraman Kalyanaraman, Milwaukee, WI (US)

(73) Assignee: MCW Research Foundation, Milwaukee, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,832

(22) Filed: Nov. 2, 1998

(65) Prior Publication Data

US 2002/0015968 A1 Feb. 7, 2002

Related U.S. Application Data

(60) Provisional application No. 60/064,025, filed on Nov. 4, 1997.

(51) Int. Cl.[7] ........................ G01N 33/53; C12Q 1/00; A01N 55/02
(52) U.S. Cl. ........................ 435/7.21; 435/4; 435/7; 435/15; 435/18; 435/21; 435/810; 435/975; 514/13; 514/326; 514/403
(58) Field of Search ................ 435/4, 18, 15, 435/21, 810, 975, 7, 7.21; 514/13, 326, 403

(56) References Cited

U.S. PATENT DOCUMENTS

| 4,571,430 A | * | 2/1986 | Byrne et al. | 560/148 |
| 4,713,366 A | * | 12/1987 | Stevens | 514/13 |
| 5,478,729 A | * | 12/1995 | Van Atta et al. | 435/7.93 |
| 5,631,127 A | * | 5/1997 | Sundrehagen | 435/4 |
| 5,998,191 A | * | 12/1999 | Tan et al. | 435/232 |

OTHER PUBLICATIONS

Shipchandler et al., Rapid fully automated measurement of plasma homocysteine with the Abbott IMx analyzer., Clinical chemistry, vol. 41, No. 7, pp. 991–994, 1995.*

Ueland et al., Total homocysteine in plasma or serum, Clinical Chemistry, vol. 39, No. 9, pp. 1764–1779, 1993.*

E. Ferguson, et al., "Generation and Initial Characterization of a Novel Polyconal Antibody Directed against Homocysteine Thiolactone-modified Low Density Lipoprotein," *J. Lipid Res.* 39:925–933, 1998.

N.P.B. Dudman, et al., "Homocysteine Thiolactone Disposal by Human Arterial Endothelial Cells and Serum In Vitro," *Arteriosclerosis and Thrombosis* 11 (3) :663–670, 1991.

F. Frantzen, et al., "Enzyme Conversion Immunoassay for Determining Total Homocysteine in Plasma or Serum," *Clin. Chem.* 44 (2) :311–316, 1998.

(List continued on next page.)

*Primary Examiner*—Christopher L. Chin
*Assistant Examiner*—Lisa V. Cook
(74) *Attorney, Agent, or Firm*—Quarles & Brady LLP

(57) ABSTRACT

An antibody specific for homocystamide adducts is disclosed. In a preferred embodiment of the present invention, the antibody is used to evaluate the level of homocysteine in a biological sample.

7 Claims, 15 Drawing Sheets

OTHER PUBLICATIONS

H. Jakubowski, "Metabolism of Homocysteine Thiolactone in Human Cell Cultures," *J. Biol. Chem.* 272 (3) : 1935–1942, 1997.

E.L. Mayer, et al., "Homocysteine and Coronary Atherosclerosis," *JACC* 27 (3) :517–527, 1996.

K.S. McCully, "Chemical Pathology of Homocysteine I. Atherogenesis," *Annals Clin. Lab. Sci.* 23 (6) :477–493, 1993.

K.S. McCully, "Homocysteine, Folate, Vitamin $B_6$, and Cardiovascular Disease," *JAMA* 279 (5) :392–393, 1998.

S.E.S. Miner, et al., "Clinical Chemistry and Molecular Biology of Homocysteine Metabolism: An Update," *Clin. Biochem.* 30(3) :189–201, 1997.

H. Refsum and S.E. Vollset, "Homocysteine and Cardiovascular Disease," *Annu. Rev. Med.* 49:31–62, 1998.

T.H. Rosenquist, et al., "Homocysteine Induces Congenital Defects of the Heart and Neural Tube: Effect of Folic Acid," *Proc. Natl. Acad. Sci. USA* 93:15227–15232, 1996.

M.T. Shipchandler and E.G. Moore, "Rapid, Fully Automated Measurement of Plasma Homocyst (e) ine with the Abbott $IMx^{200}$ Analyzer," *Clin. Chem.* 41 (7) :991–994, 1995.

P.M. Ueland, et al., "Total Homocysteine in Plasma or Serum: Methods and Clinical Applications," *Clin. Chem.* 39(9) :1764–1779, 1993.

G.N. Welch and J.Loscalzo, "Mechanisms of Disease: Homocysteine and Atherothrombosis," *New Eng. J. Med.* 338(15) :1042–1050, 1998.

* cited by examiner homocysteine
thiolactone

N-acetyl homocysteine
thiolactone methanethiosulfonate
spin label

MTSL-labeled
homocystamide-
LDL adduct

A

B

IMMONOLOGICAL DETECTION OF THE HOMOCYSTAMIDE ADDUCT AND A THIOLACTONE IMMUNOASSAY FOR ENDOGENEOUS HOMOCYSTEINE

CROSS-REFERENCE TO RELATED APPLICATION

This application claims priority from U.S. Ser. No. 60/064,025, filed Nov. 4, 1997.

STATEMENT REGARDING FEDERALLY SPONSORED RESEARCH OR DEVELOPMENT

This invention was made with U.S. government support awarded to the following agency: NIH grants HL47250 and RR01008. The U.S. has certain rights in this invention.

BACKGROUND OF THE INVENTION

Homocysteinemia is defined as the presence of the amino acid homocysteine in the blood. Although homocysteine is normally present in the blood of healthy humans at concentrations of 3–5 $\mu$M, homocysteinemia generally refers to the medical condition of hyperhomocysteinemia, a situation in which plasma homocysteine concentrations are elevated (62, 84, 108). It has been proposed to classify homocysteinemia as moderate (15–30 $\mu$M), intermediate (30–100 $\mu$M), and severe (>100 $\mu$M) on the basis of fasting plasma homocysteine concentrations (50).

Elevated levels of plasma homocysteine (homocysteinemia) are present in several pathologies (2, 6–7, 17, 30, 33, 35, 47, 50, 52–53, 59, 62–67, 68–70, 72–76, 81–84, 96, 105, 107–111, 114–116, 118, 121). The precise mechanisms by which homocysteinemia is related to the etiology of disease remains unknown. Inborn errors of amino acid metabolism in the transulfuration and remethylation pathways (In the metabolism of sulfur-containing amino acids, homocysteine is formed under physiological conditions by the demethylation of methionine. Homocysteine can either be remethylated by methylfolate homocysteine methyltransferase, or it may proceed to be converted to cystathionine and then to cysteine by the sequential actions of the enzymes cystathionine $\beta$-synthase (CBS) and cystathionase, respectively). For many years, deficiencies of these enzymes have been recognized in children to cause homocysteine to be excreted in the urine (homocysteinuria). Children suffering from this rare genetic condition rarely survive into adulthood and develop atherosclerosis and thromboembolic disorders (9, 89). Recently, it has been shown that another genetic cause of homocysteinemia is a mutation of the methylfolate homocysteine methyltransferase gene (25–26, 83, 118). Certain of these individuals appear to be susceptible to the development of premature vascular disease. Despite the plethora of epidemiological evidence linking homocysteinemia to the development of atherosclerosis and thromboembolic disorders, the role of homocysteine in these conditions remains unclear.

The cyclic thioester, homocysteine thiolactone, has been implicated as a compound, which may be formed in conditions of homocysteinemia (equation 1) (63–67). Homocysteine thiolactone has been shown to react with primary amines by forming an amide linkage (equation 2) (1). Once formed in aqueous solution at physiological pH and temperature, homocysteine thiolactone is stable with a half-life of 25 hours (45). The half-life will decrease, however, in the presence of primary amines. For example, in the presence of excess cysteine, or lysine, the half-life is reported to be 3 hours (45). In addition, the reactivity of homocysteine thiolactone toward primary amines will increase at a higher pH (e.g. 8.0–8.4). However, it has been demonstrated that this molecule is unstable at high pH and will hydrolyze to form homocysteine (13). It has been reported that homocysteine thiolactone is capable of modifying LDL to a form which is capable of generating foam cells (72). While there is evidence that indicates homocysteine thiolactone may be involved in atherosclerosis, arteriosclerosis, and thromboembolic disorders, a method for the detection of the homocystamide adduct has been lacking.

Autoantibodies recognizing oxidized LDL, malondialdehyde-lysyl-LDL adduct, or 4-hydroxynoneal-lysyl-LDL adduct have been found to occur in vivo (8, 77, 120). In addition, derivitization of albumin, fibrinogen, or LDL lysyl residues by carbamylation, acetylation, ethylation, and methylation has been shown to result in high affinity antibodies directed against these modifications in experimental animals (99). These studies show that LDL may be a good carrier molecule for the immunization of animals (99). It has been suggested that analogous biochemistry between homocysteine thiolactone and LDL, resulting in homocystamide-LDL adducts, could result in the formation of autoantibodies against these adducts, although the notion of homocysteine thiolactone in vivo was considered physiologically irrelevant (equation 3, FIG. 1A) (14–15).

BRIEF SUMMARY OF THE INVENTION

In one embodiment, the present invention is an antibody or a portion thereof which specifically forms a complex with a homocystamide adduct. The antibody may be either a monoclonal or polyclonal antibody and the homocystamide adduct is preferably selected from the group consisting of homocystamide-LDL, homocystamide-BSA and homocystamide-lysine.

Preferably, the affinity of the antibody for the homocystamide adduct is at least such that the $IC_{50}$ is less than 15 $\mu$M.

In another embodiment, the present invention is a method of measuring homocysteine levels in the sample comprising the steps of obtaining the sample, treating the sample such that endogenous homocysteine is converted to homocystamide adduct of either exogenous or endogenous carrier molecules, exposing the sample to the antibody described above, and correlating the binding of the antibody to a standard antibody binding profile. In this way, one may measure homocysteine levels in samples such as human plasma.

The present invention is also a method of evaluating endogenous homocystamide adducts comprising the steps of obtaining the sample, exposing the sample to the antibody of claim 1 and correlating the antibody binding to a standardized antibody binding profile.

It is an object of the present invention to measure homocysteine levels in both biological and non-biological samples.

It is another object of the present invention to diagnostically predict a patient's susceptibility to vascular occlusive disorders.

It is another object of the present invention to evaluate the endogenous homocystamide adduct level in biological and non-biological samples.

It is another object of the present invention to provide an antibody specific for homocystamide adducts.

Other objects, advantages and features of the present invention will become apparent to one of skill in the art after one has evaluated the specification, claims and drawings.

DESCRIPTION OF THE SEVERAL VIEWS OF THE DRAWINGS

FIG. 3A is a control, MTSL-labeled native LDL.

In FIG. 9A, homocysteine (75 μM) was incubated at 25° C. in the presence of HCl (6N), DTT (1 mM), and DTPA (100 μM). The absorbance (minus the blank consisting of the above mixture in the absence of homocysteine) was measured in a quartz cuvette every hour for 14 hours. Solid traces (240 nm maxima) indicate increasing concentrations of homocysteine thiolactone.

FIGS. 10D–F is as FIGS. 10A–C, but homocysteine thiolactone (2 mM), homocysteine (2 mM), or PBS was pre-treated with HCl (6N) for 2 hours at 60° C. and subsequently neutralized with NaOH (6N)/borate (1 M, pH 8.4) so that the final pH was 8.4 prior to incubation with BSA. ESR conditions: scan range, 100 G; scan field, 3368 G; modulation amplitude, 1.0 G; modulation frequency, 9.4 GHz; scan time, 0.5 minutes; time constant, $0.034s^{-1}$ microwave power, 20 mW.

FIG. 13A: As shown, homocysteine is coupled to a carrier molecule by the intermediate formation of homocysteine thiolactone.

DETAILED DESCRIPTION OF THE INVENTION

1. In General

A. Abbreviations

Figure 1A:
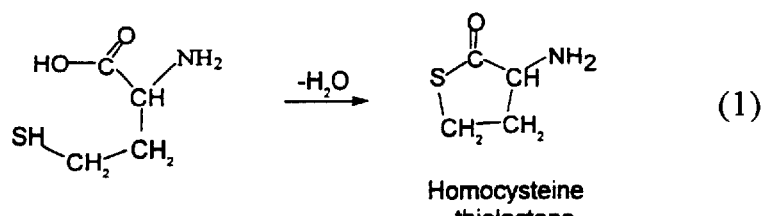
FIGS. 1A and B depict chemical structures and equations useful in the present invention.
Figure 1A:
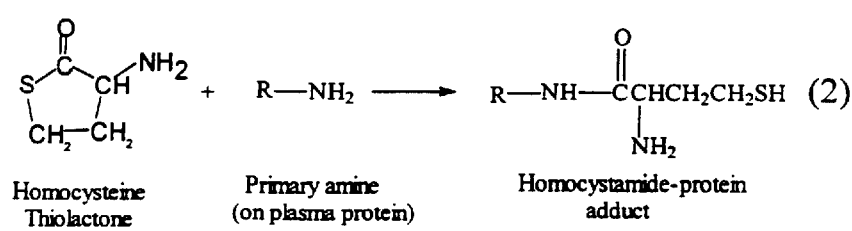
Figure 1A:
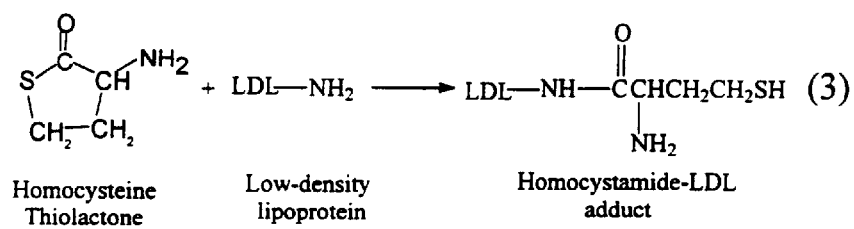
Figure 1A:
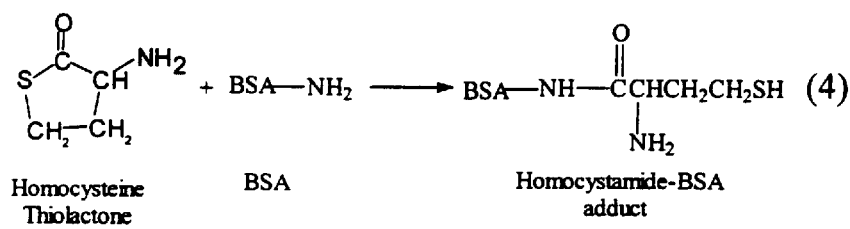
Figure 1A:
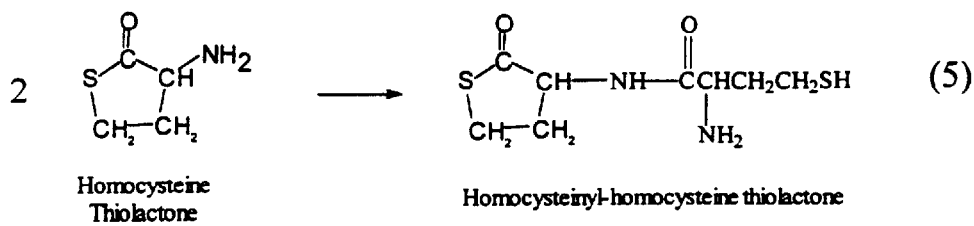
Figure 1A:
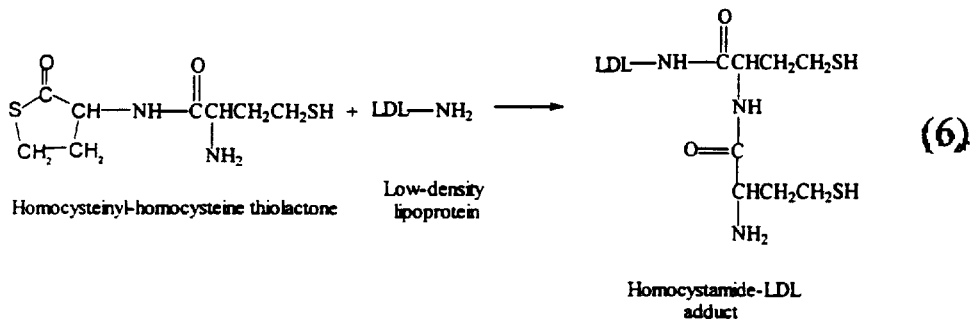

The following is a list of abbreviations used in this application: LDL, low-density lipoprotein (1.019–1.063 g/ml); HDL, high-density lipoprotein (1.063–1.21 g/ml); LPDS, liporotein-deficient serum (>1.21 g/ml); apo-B, apolipoprotein B-100; EDTA, ethylenediaminetetraacetic acid; DTPA, diethylenetriaminepentaacetic acid; BHT, butylated hydroxytoluene; REM, relative electrophoretic mobility; $IC_{50}$, 50% inhibitory concentration; TNBS, 2,4,6-trinitrobenzenesulfonic acid; DTNB, dithio-bis-2-nitrobenzoic acid; ELISA, enzyme-linked immunoadsorbent assay; TMB, $3,3^N,5,5^N$-tetramethyl benzidine substrate solution; SDS, sodium dodecyl sulfate; Tween-20, polyethylenesorbitan monolaurate; PBS, phosphate buffered saline; BSA, bovine serum albumin; NEM, N-ethylmaleamide; ESR, electron spin resonance; MTSL, methanethiosulfonate spin label; CROX, potassium chromium (III) oxalate trihydrate; KLH, keyhole limpet hemocyanin.

B. Homocysteinemia

Elevated plasma homocysteine concentrations (homocysteinemia) are presumed to be responsible for the development of a number of diseases, including vascular occlusive disorders. However, it is unclear precisely how homocysteinemia is related to the etiology of disease. Homocysteine thiolactone is a cyclic thioester that is implicated in the development of vascular disease. This molecule will readily acylate primary amines, forming a homocystamide adduct, which contains a primary amine and a thiol.

C. Embodiments Presented in the Examples

In the Examples below we have characterized the homocystamide-low-density lipoprotein (LDL) adduct, a product of the reaction between homocysteine thiolactone and LDL. Treatment of LDL with homocysteine thiolactone resulted in a time-dependent increase in LDL-bound thiols that reached approximately 250 nmol thiol/mg LDL protein. The thiol groups of the homocystamide-LDL adduct were labeled with the thiol-reactive nitroxide, methanethiosulfonate spin label. Using paramagnetic relaxing agents and the electron spin resonance spin labeling technique, we determined that the homocystamide adducts were predominately exposed to the aqueous phase. We conclude that the reaction between homocysteine thiolactone and LDL generates a modified LDL molecule in which homocysteine is bound to lysyl residues of apolipoprotein B-100 by a peptide bond.

We also examined the possibility that this adduct was immunogenic. New Zealand White Rabbits were immunized with this adduct at 6-week intervals. Antisera collected following the $3^{rd}$ immunization was assayed for antibody titers using solid phase ELISA techniques. Titers (defined as the inverse of the greatest serum dilution in which there was a significant difference (p<0.05) between the percentage antibody bound from the antiserum and the pre-immune serum) were approximately $10^5$. In competition-based ELISAs, homocysteine thiolactone-treated LDL competed for binding with the antiserum, as the 50% inhibitory concentration was approximately 10 μg/ml. Neither homocysteine, homocystine (homocysteine disulfide), nor $Cu^{2+}$-oxidized LDL competed for binding. LDL in which lysyl residues were derivatized by acetylation or methylation were not recognized by the antiserum. Homocysteine thiolactone-treated plasma competed for binding to the antiserum, whereas native plasma did not. All lipoprotein fractions from the homocysteine thiolactone-treated plasma competed for binding to the antiserum. We conclude that homocysteine thiolactone-modified LDL is highly immunogenic. The antiserum obtained is highly specific for homocysteine thiolactone-modified lysines.

In the Examples below, we also describe a procedure for the preparation of a homocysteine-bound antigen column and subsequent immunoaffinity purification of the polyclonal antibody. The antibody was purified using ammonium sulfate precipitation of total serum antibodies. These antibodies were bound to the antigen column, washed, and eluted. The purified antibodies were concentrated to 0.55 mg/ml. The predominant immunoglobulin class in the purified antibody solution, as determined by immunoglobulin-specific secondary antibodies, was IgG. The purified antibody was directed against the homocystamide-LDL adduct but not native LDL, as determined by competition ELISA. In addition, homocystamide adducts of bovine serum albumin, keyhole limpet hemocyanin, and hemoglobin were recognized. Homocystine (homocysteine disulfide) was recognized, however with much lower affinity. Western blotting data demonstrate that the homocystamide-protein adduct may be identified using this technique.

In order to show the usefulness of this invention for measuring homocysteine concentrations in humans, the chemistry of homocysteine and homocysteine thiolactone was investigated. The rate of HCl-mediated dehydration of homocysteine to homocysteine thiolactone was investigated by monitoring the absorbance at 240 nm. In the presence of 6N HCl, at 25° C. the kinetics of homocysteine thiolactone formation were slow, as efficient conversion did not occur until 12 hours. However, if the temperature was raised to 60°, efficient conversion occurred within 2 hours. Normal human plasma was spiked with homocysteine, and it was demonstrated that homocysteine thiolactone could be formed stoichiometrically. Using the thiol-reactive nitroxide, MTSL, and the ESR spin labeling technique, it was demonstrated that homocyteine could be bound to BSA, presumably by the intermediate conversion to homocysteine thiolactone and subsequent acylation of BSA lysyl residues. Using solid phase ELISA techniques, it was demonstrated that homocysteine could be quantitatively analyzed in human plasma containing known concentrations of homocysteine. The potential for using this antibody as a diagnostic tool for measuring plasma homocysteine concentrations and its implications for understanding diseases induced by or found in association with homocysteinemia are discussed below.

D. Thiolactone Immunoassay

Figure 13:
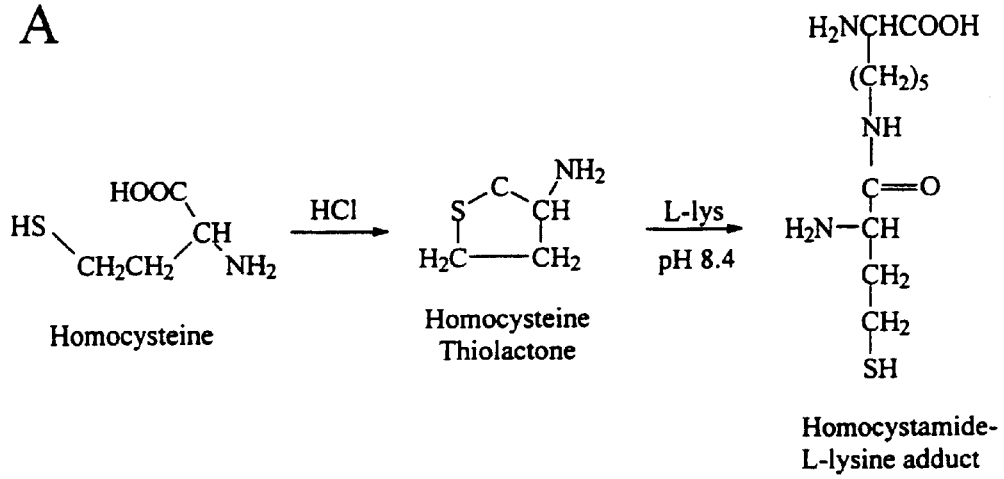
FIGS. 13A and B are diagrams of the measurement of homocysteine by ELISA.
FIG. 13B: In a competitive ELISA, the test solution (or standard) described in FIG. 13A is incubated with antibodies directed against the homocystamide adduct. Antibody bound to the solid phase is measured using a secondary antibody bound to horseradish peroxidase. TMB is added as a substrate, and measured at 450 nm.
Figure 13:
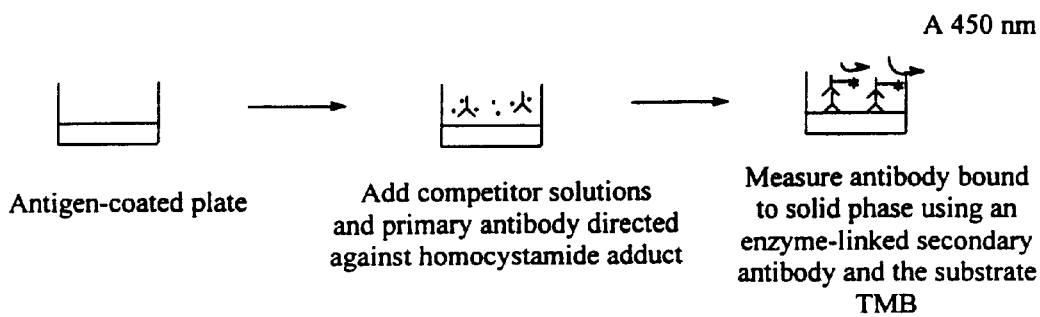

The present assay, hereafter referred to as the "Thiolactone Immunoassay," is used for the detection and measurement of homocysteine. FIG. 13 is an example of one embodiment of the thiolactone immunoassay. The method comprises a chemical procedure in which a sample is coupled to a carrier molecule that contains primary amines. Subsequently, the coupled sample (a "homocystamide adduct") is exposed to an antibody specific for homocystamide adducts, such as the antibody described below. One may then calculate the plasma homocysteine concentration from an antibody-binding profile.

The sample to be assayed may be either biological or non-biological. Preferably, the sample is human plasma. Other examples of preferred samples include human tissue homogenates (e.g., heart, brain, blood vessels, liver), animal tissue, bacterial tissue, cell culture tissue, urine, synovial fluid, all bodily fluids or food products (e.g., fruit juice).

The aqueous sample is typically treated such that endogenous homocysteine is converted to homocystamide adduct of either exogenous or endogenous carrier molecules. Depending on the sample to be assayed, one may include a chemical reduction that would be capable of releasing any oxidized homocysteine prior to the formation of homocystamide adduct.

For example, in a human plasma specimen, an aliquot of plasma is treated with a reducing agent, preferably dithiothreitol or tributylphosphine, thus releasing "total" plasma homocysteine (endogenous homocystamide adducts, if present, are not released by reduction). The sample is then preferably subjected to ultrafiltration, and the homocysteine in the ultrafiltrate is converted chemically, by dehydration, to homocysteine thiolactone. Alternatively, homocysteine may be converted enzymatically to homocysteine thiolactone (43–46). Subsequently, homocysteine thiolactone is coupled, preferably to an exogenous lysine. Preferably, the carrier molecule is L-lysine. However, other carrier molecules will function equally well.

The Examples below describe particular preferable methods of converting endogenous homocysteine in a sample into homocystamide adducts.

The resulting product (homocystamide adduct of lysine carrier molecule) is detected, preferably using the immunoassay described below. The concentration of homocysteine is determined by a standard curve of homocystamide adducts prepared in parallel with the test specimen.

As with the preparation of the immunogen (described below), the homocystamide adduct is a requirement in the measurement of homocysteine concentrations. It may be possible to produce the homocystamide adduct by many methods that may or may not involve a homocysteine thiolactone intermediate. It is the product, the homocystamide adduct, that is of significance-irrespective of the route by which it was produced. We speculate that non-thiolactone homocysteine derivatives (chemical or metabolic) may be used to produce the homocystamide adduct.

The homocysteine concentration can be correlated to various disease states including vascular disease (e.g., coronary artery disease, peripheral vascular disease, cerebral vascular disease) and consequences thereof (e.g., myocardial infarction, aortic aneurysms, stroke); neurodegenerative diseases; Alzheimer's disease; renal failure; hypertension; hyperlipidemia; neural tube defects (e.g., spina bifida) in children of homocysteinemic mothers; systemic lupus erethematosus; dibetes mellitus; sickle cell anemia; genetic mutations or deficiencies in the transsulfuration and remethylation pathways of amino acid metabolism (e.g., cystathionine-β-synthase) and in the folate cycle (e.g., methylene tetrahydrafolate reductase), and poor nutritional status (deficiencies of vitamins $B_6$, $B_{12}$, or folate). This also includes gastrointestinal resection patients, chronic alcoholics, vegetarians, patients receiving chemotherapy (e.g., anti-folate drugs), and patients receiving treatment for Mycobacterium tuberculosis (e.g., $B_6$-antagonists such as Isoniazid).

E. Homocystamide-Specific Antibodies

The present invention is also an antibody specific for metabolic products of homocysteine, particularly homocystamide adducts.

In one embodiment, this antibody is created as described below by immunizing New Zealand White rabbits with the product formed from the reaction of homocysteine thiolactone and apolipoprotein B-100 lysyl residues of homologous low-density lipoprotein (LDL). We speculate, however, that specific antibodies—either polyclonal or monoclonal—may be obtained by immunizing other animals (e.g., mice, goats, pigs, donkeys) in a similar manner with the above stated immunogen. In addition, carrier molecules other than homologous LDL (e.g., ovalbumin, thyroglobulin, keyhole limpet hemocyanin) may be employed.

For the preparation of antibodies directed against the homocystamide adduct, it is necessary to obtain or produce homocystamide adducts that can be administered to animals. The key structural feature of the homocystamide adduct is homocysteine, which is linked by a nitrogen atom of an adjacent molecule or chemical group to the carbonyl group of homocysteine. This is referred to as an amide bond.

By "homocystamide adduct" we mean that homocysteine is bound to another molecule by an amide bond, although the term "homocystamide adduct" refers structurally to the homocysteine portion of the combination. "Homocystamide adduct" also implies that homocysteine is bound to another molecule, however, the adduct is promiscuous, as it may bind a number of different molecules. In addition, such homocystamide adducts may be both polymeric or monomeric, as homocystamide adducts may react with each other. The adducts have sulfhydryl groups, which may or may not be cross-linked. Preferably, the homocystamide adduct is attached to a carrier molecule. It is likely that the homocystamide adducts will lie in aqueous environments (as opposed to hydrophobic), although this is not necessarily always true. This can be determined by the electron spin resonance (ESR) spin labeling technique.

Preferably, the homocystamide adduct is prepared from some form of homocysteine. For example, one may use homocysteine thiolactone (The free base or the hydrochloride salt may be used. In addition, the D-, L-, or D,L-forms may be used. A catalyst such as a heavy metal may or may not be employed). If starting from homocysteine thiolactone, the compound is reacted with the carrier molecule.

The carrier molecule is preferably homologous low-density lipoprotein (LDL). Other carrier molecules are possible, however, e.g., autologous LDL, heterologous LDL, bovine serum albumin (BSA), ovalbumin, thyroglobulin, and keyhole limpet hemocyanin (KLH). In addition, it is possible that synthetic, non-biological carrier molecules may be employed.

After incubation, any excess homocysteine thiolactone is separated from the carrier molecules, which contain bound homocystamide adducts following incubation. It may not be necessary to begin with homocysteine thiolactone as a starting compound, however. The end product, however, should be the homocystamide adduct. For example, it is possible that an immunogen prepared may be slightly different than the homocystamide adduct if the immunogen is modified either chemically or metabolically following administration to the animal. It is also possible that the homocystamide adduct may be prepared by other enzymatic or chemical processes.

For the production of antibodies—which may be either monoclonal or polyclonal—an immunogen (described above) is administered to an animal (route of administration may be via a number of ways such as subcutaneous, intradermal, intraperitoneal, etc.) according to standard protocols. Preferably, the animal is a New Zealand White Rabbit, but one may use other animals (e.g., mice, sheep, pigs, goats, donkeys). It is preferable that the immunogen is emulsified using an adjuvant, however, the use of adjuvants is not necessarily required.

Preferably, following at least two immunizations, serum is obtained from the animal and tested for specificity according to standard procedures (e.g., screen using solid phase ELISA techniques). The antiserum obtained in this case is polyclonal. This antiserum may be used as crude antiserum or may be further purified using standard procedures.

We have described a novel antigen for the purification of antiserum directed against the homocystamide adduct, namely, the preparation of a homocystamide adduct antigen column.

Preferably, homocystamide adducts are attached to a non-immunoreactive substance (e.g., aminohexylsepharose). The substance (containing bound homocystamide adducts) is poured or placed in an immunoaffinity purification setup, such as a column. Antiserum is allowed to cross-react with the column, and the specific antibodies are eluted off the antigen column according to standard protocols.

An initial step in the preparation of monoclonal antibodies directed against the homocystamide adduct is inducing a polyclonal response in an animal (e.g., mouse). This would be accomplished as described above. Hybridomas would be prepared according to standard protocols. One could obtain a number of hybridomas that would produce antibody directed against the homocystamide adduct. Monoclonal antibodies may be used in a number of forms (e.g., cell culture supernatants, ascites, etc.).

A suitable antibody for the present invention has an affinity for the homocystamide adduct such that the $IC_{50}$, is less than 15 $\mu$M.

F. Detection of Endogenous Homocystamide Adducts

The method of the present invention is capable of identifying homocystamide adducts. Thus, it is possible to measure endogenous homocystamide adducts in biological or non-biological specimens using our assay. We speculate that homocystamide adducts may be formed in such specimens. The method by which the adducts form, for example, could be via the intermediate formation of homocysteine thiolactone (e.g., by the editing action of methionyl tRNA synthetase on homocysteine). We have demonstrated that the antibody of the present invention is capable of identifying homocystamide adducts in human plasma and components thereof (e.g., low-density lipoprotein, high-density lipoprotein, lipoprotein-deficient serum). It is possible to probe other tissues for the homocystamide adduct (e.g., heart, brain, kidney, lung, liver, blood vessels, etc.).

EXAMPLES

In the Examples, below, we describe the preparation and synthesis of the homocystamide-LDL adduct (21). In addition, the structural aspects of this adduct have been characterized using the Ellman's Reagent and the electron spin resonance (ESR) spin labeling technique (21). Results indicate that homocysteine can be bound to apolipoprotein B-100 (apo-B) lysyl residues by a peptide bond (21). In addition, we assessed for the first time the possibility that the homocystamide-LDL adduct was immunogenic (23). We have raised in rabbits a polyclonal antibody directed against the homocystamide-LDL adduct (23). In the Examples, we have characterized the specificity of this polyclonal antiserum for the recognition of homocystamide-protein adducts.

In general, the use of polyclonal antiserum may be problematic due to binding of a repertoire of nonspecific antibodies collected from an animal's serum. Typically, this is overcome in a few ways. In some cases, high concentrations of blocking buffers may lower nonspecific binding. We sought to purify the anti-homocystamide adduct antibody using an antigen column, which was prepared by the incubation of homocysteine thiolactone with agarose beads bound by a 12-carbon spacer to a terminal amino group (aminohexylsepharose). Using common immunoaffinity techniques, this antigen column was used for antibody purification. Following purification, the polyclonal antibody was characterized using solid phase ELISA and Western blotting techniques.

Development of techniques for measuring plasma homocysteine concentrations is an active area of research, as homocysteinemia is associated with the development of a number of pathologies, such as neurodegenerative diseases, Alzheimer's disease, neural tube defects, diabetic neuropathy, systemic lupus erethematosus, renal failure, and rheumatoid arthritis (17, 30, 47, 73, 81–82, 86, 104, 113). In addition, a number of vascular-occlusive disorders are attributed to homocysteinemia (5, 6, 28, 62). Conversely, reduction of previously elevated plasma homocysteine concentrations has been shown to be associated with a decreased risk for the development of many of these vascular disorders (111). Vascular disease is a leading cause of mortality in Western countries (58). While measurement of plasma homocysteine levels is generally restricted to research laboratories, it is likely that routine measurement of plasma homocysteine concentrations will be part of the clinical domain in the near future (118). An antibody-based assay for plasma homocysteine has previously been described, but is not commercially available in the U.S. at this time (91). This assay relies on the reversible enzymatic conversion of homocysteine to S-adenosyl homocysteine and subsequent measurement with an antibody directed against S-adenosyl homocysteine in an enzyme-linked immunoassay (ELISA) (27, 91). Here, we have developed an alternative immunoassay, which is based on the irreversible non-enzymatic binding of homocysteine to a primary amine-containing carrier molecule and subsequent measurement with an antibody directed against homocystamide adducts using an ELISA. Our immunological approach may be advantageous, as sample treatment is simple and does rely on enzymes and/or enzyme inhibitor solutions for homocysteine coupling, as in the previously described immunoassay (27, 91). Sample treatment requires binding of homocysteine to a carrier molecule (e.g. BSA) and can be readily accomplished by the HCl-mediated conversion of homocysteine to the corresponding thiolactone (eq. 1, FIG. 1A) and subsequent incubation with the carrier molecule, forming a homocystamide adduct (e.g., eq. 4, FIG. 1A, using a BSA carrier molecule).

We also investigated the efficiency of the dehydration of homocysteine to the corresponding thiolactone (eq. 1, FIG. 1A). Additionally, coupling of homocysteine to BSA (eq. 4, FIG. 1A) was verified using a thiol-reactive spin label and electron spin resonance. Measurement of homocysteine in human plasma samples was accomplished with a competition ELISA and standards consisting of homocystamide adducts. Results indicate that the present immunoassay can measure homocysteine in human plasma. We conclude that this approach is useful for the detection and measurement of homocysteine in biological specimens in general.

In addition, we speculate that this technique may be used to probe biological tissue for homocystamide aducts formed from endogenous homocysteine thiolactone. We believe that this is the first reported method for the unequivocal detection of the homocystamide adduct.

1. Materials and Methods

New Zealand White Rabbits were supplied by New Franken Research Rabbits (New Franken, Wis. and 96-well polystyrene plates were obtained from Corning (Corning, N.Y.). Horseradish peroxidase-labeled goat-anti-rabbit IgG (heavy chain-specific) and -$\mu$-chain specific IgG were obtained from Bethyl Laboratories (Houston, Tex.). Horseradish peroxidase-labeled goat-anti-rabbit IgG (heavy and light chain-specific), $3,3^N,5,5^N$-tetramethyl benzidine substrate solution (TMB), Supersignal Chemiluminescent Substrate, keyhole limpet hemocyanin (KLH), and 2,4,6-trinitrobenzenesulfonic acid (TNBS) were supplied by Pierce (Rockford, Ill.). Freund's adjuvant was obtained from Gibco BRL (Grand Island, N.Y.). Dithio-bis-2-nitrobenzoic acid (DTNB), $\omega$-aminohexylsepharose, potassium bromide, Folin and Ciocalteu's Phenol Reagent, guanidine hydrochloride, sodium dodecyl sulfate (SDS), Sephadex G-25, polyoxyethylenesorbitan monolaurate (Tween-20), ethylenediaminetetraacetic acid (EDTA), butylated hydroxytoluene (BHT), materials for all phosphate buffered saline (PBS, sodium phosphate [25 mM], sodium chloride [125 mM], pH 7.4), homocysteine thiolactone hydrochloride, homoserine lactone hydrobromide, N-acetyl-homocysteine thiolactone, and homocystine were obtained from Sigma Chemical Co. (St. Louis, Mo.). Sodium nitrite, sodium tartrate, sodium hydroxide, diethylenetriaminepentaacetic acid (DTPA), sulfuric acid, and methylene chloride were purchased from Fisher Scientific (Itasca, Ill.). Materials for polyacrylamide gels and Western blotting (Mini-Protean II electrophoretic cell, acrylamide, bis-acrylamide, TEMED, ammonium persulfate, filter paper and pads, nitrocellulose) were obtained from BIO-RAD Laboratories (Hercules, Calif.). Centriprep protein concentrators were purchased from Amicon (Beverly, Mass.). 96-well Multiscreen plates were obtained from Millipore (Bedford, Mass.). Formaldehyde, acetic anhydride, potassium chromium (III) oxalate trihydrate (CROX), and hydroxylamine hydrochloride were purchased from Aldrich Chemical Co (Milwaukee, Wis.). Methanethiosulfonate spin label (MTSL) was synthesized as described previously (3).

LDL (1.019–1.063 g/ml), high-density lipoprotein (1.063–1.21 g/ml, HDL), and lipoprotein-deficient serum proteins (>1.21 g/ml, LPDS) were isolated from plasma by sequential ultracentrifugation through a potassium bromide gradient (36). LDL protein concentrations were measured by the Lowry assay (60). The freshly prepared LDL was stored under argon at 4° C. in PBS containing EDTA (1 mM) and was used within 2 weeks of preparation in order to exclude the possibility of generating antibodies against oxidized LDL.

Preparation of homocystamide-LDL adducts.

Homocystamide-LDL adducts were prepared by the addition of LDL (~2–10 mg in PBS containing 100 $\mu$M DTPA) to freshly extracted homocysteine thiolactone free base. The mixture was incubated with gentle stirring for the indicated times and passed through a Sephadex G-25 column in order to separate the unreacted homocysteine thiolactone. Protein and thiol concentrations were determined following this reaction.

Other Modifications of LDL Lysyl Residues.

Acetylation of LDL was performed as described elsewhere (99). This modification was assessed qualitatively by agarose gel electrophoreseis using a Paragon Lipogel electrophoresis apparatus (40). LDL (5 $\mu$g) was loaded onto the gel and subjected to electrophoresis for 30 minutes at 150 V. The mobility of native LDL was compared to acetylated LDL. Reductive methylation was done as described previously (7), and the extent of methylation was measured using the TNBS assay (100) with an extinction coefficient ($\epsilon$=3,800 $M^{-1}$ $cm^{-1}$) determined from a standard curve using valine.

Thiol determinations. Protein thiol groups in LDL samples were assayed using the DTNB reagent (Ellman's reagent) (85). An extinction coefficient ($\epsilon$=11,000 $M^{-1}$ $cm^{-1}$) was determined from a standard curve generated using reduced cysteine and was used for all calculations. Thiol concentrations are given in terms of nmol per mg LDL protein. Plasma homocysteine was measured by HPLC as previously described, except that tributyplphosphine reduction was not employed (24). In this manner, "free" plasma homocysteine is measured.

Spin labeling and electron spin resonance. Samples were labeled for 1 hour at 25° C. using a concentrated solution of MTSL (500 mM in acetonitrile). Excess spin label was removed from samples by bucket desalting in columns pre-equilibrated with PBS and DTPA (100 $\mu$M). ESR spectra were recorded using a Varian E-109 Century Series spectrometer. Samples for spin-labeling experiments were placed in a quartz flat cell for a $TE_{101}$ cavity.

Preparation of immunogen (homocystamide-LDL adducts) and immunization of animals. Homocystamide- LDL adduct was prepared by the addition of homologous LDL (~2–10 mg in phosphate buffer containing 100 μM DTPA) to homocysteine thiolactone free base. The mixture was incubated for 30 minutes with gentle stirring on ice and passed through a Sephadex G-25 column in order to separate the unreacted homocysteine thiolactone. The percentage of apo-B lysyl residues which reacted with homocysteine thiolactone was quantified by measuring the increase in protein thiols using the DTNB assay (22, 85), as the reaction between homocysteine thiolactone and a primary amino group generates a thiol (equation 2, FIG. 1A). Using these conditions, consistently 30–40% of apo-B lysyl residues reacted with homocystine thiolactone to form homocystamide-LDL adducts (assuming 500,000 molecular weight for apo-B and 180 lysyl residues per apo-B molecule) (18). The immunogen was prepared as described within 24 hours of each of the immunizations. Homocystamide adducts of BSA and of hemoglobin were prepared using the same conditions that were used for the preparation of homocystamide-LDL adduct.

Two 1.8 kg female New Zealand White Rabbits were immunized using standard protocols (34) and in accordance with the guidelines of the Medical College of Wisconsin Animal Care Committee. Prior to the first immunization, 10 ml serum was collected from each rabbit to serve as negative controls. In an equal volume of complete Freund's adjuvant, 0.5 mg homocystamide LDL adduct was emulsified so that the final volume was ~1 ml. This was injected in multiple subcutaneous sites. Serum was collected 7 days later and was tested for antibody titers. Subsequent immunizations were spaced at 6-week intervals following the injection, but incomplete Freund's adjuvant was used for emulsification of the immunogen.

Solid phase ELISA techniques for antibody characterization. Solid phase indirect antibody capture techniques were used in all assays and have been described elsewhere (10, 34). Briefly, 96-well plates were initially coated with homocystamide-LDL adduct (100 μl, 10 μg/ml). For antibody titer determinations, the antisera were diluted at concentrations as indicated in the "Results" section. We defined antibody titers as the inverse of the greatest serum dilution in which a significant difference ($p<0.05$) between the percentage antibody bound from the antiserum and the pre-immune serum was observed. Immunoglobulin classes were determined using goat-anti-rabbit-$\mu$-chain-specific, -heavy chain specific, and -heavy and light chain specific secondary antibodies that were linked to horseradish peroxidase. In order to determine antibody specificity, competition experiments were employed, using a limiting dilution (1:300) of purified antibody. Horseradish peroxidase-labeled goat-anti rabbit (heavy and light chain-specific) was used as a substrate, and the reaction was quenched by the addition of $H_2SO_4$ (100 μl, 1.8 M). The absorbance was measured at 450 nm in a 96-well plate reader.

Antigen column preparation. ω-Aminohexylsepharose was coupled to homocysteine thiolactone by the addition of homocysteine thiolactone free base (1.5 mg) to 15 of the sepharose beads in a PBS slurry. The mixture was stirred gently for 1 hour at 25° C., after which the beads were washed once with PBS and subsequently incubated for 4 hours at 25° C. in 10 volumes of ethanolamine (100 mM, pH 7.5) with gentle mixing. The beads washed twice with PBS. Coupling was verified qualitatively by the increased thiol content as measured by the DTNB assay.

Purification of antiserum. Polyclonal rabbit-anti-homocystamide antiserum was obtained following the 4th immunization of New Zealand White rabbits with homologous homocystamide-LDL adduct (0.5 mg in Freund's adjuvant) as described previously (34). A saturated solution of ammonium sulfate was added dropwise to the antiserum while stirring until the solution was 25% saturated with ammonium sulfate. This mixture was incubated overnight at 4° C. The mixture was centrifuged, and pellet was discarded. Ammonium sulfate was added to the supernatant while stirring until the final concentration of the solution was 50% ammonium sulfate. This mixture was incubated overnight at 4° C. The mixture was centrifuged, and the supernatant was discarded. The pellet was brought up in and dialyzed against Tris (10 mM, pH 7.5).

The ammonium sulfate-purified polyclonal antibody solution was further purified with the antigen column using commonly employed immunoaffinity purification techniques (34). Specifically, the polyclonal antibody solution was passed 3 times through a 15-ml antigen column. The column was washed with 20 bed volumes of Tris (10 mM, pH 7.5) and 20 bed volumes of sodium chloride (500 mM)/Tris (10 mM, pH 7.5). Antibodies were eluted from the column with 10 volumes of glycine (100 mM, pH 2.5) and collected into 1 volume of Tris (1 M, pH 8.0). The eluted antibody solution was subsequently concentrated to 0.55 mg/ml and dialyzed against PBS.

SDS PAGE and Western blots. SDS PAGE was performed on 5% continuous separating gels (54). Western blotting was performed as previously described (106).

Homocysteine thiolactone determination. Homocysteine thiolactone was measured at 240 nm, as previously described (16). Concentrations were calculated using a standard curve of authentic homocysteine thiolactone.

Assay Methods for Plasma Homocysteine

Microtiter plate preparation. BSA (10 mg/ml in 1M borate, pH 8.4) was incubated for 6 hours at 25° C. in the presence of homocysteine thiolactone (50 mM). Following incubation, excess homocysteine thiolactone was removed by passing the sample down a column pre-equilibrated with $NaCO_3$ (100 mM, pH 9.6). Homocystamide-BSA adduct was diluted to 5 μg/ml in $NaCO_3$ (100 mM, pH 9.6), and 200 μl/well was added to polystyrene microtiter plates (11). These plates were incubated overnight at 4° C., rinsed in PBS, and either used immediately or covered and stored in PBS for future use.

Preparation of a standard curve. In order to prepare a standard curve of known homocysteine concentrations, the indicated concentrations of homocysteine were incubated in the presence of HCl (6N) and heated at 60° C. for 2 hours. By this procedure, homocysteine undergoes a dehydration reaction, thus forming homocysteine thiolactone (13). Following this process, the pH of the samples were adjusted to 8.4 by first adding borate buffer (1M, pH 8.4) and next NaOH (6N). Each sample was vortexed immediately following the addition of these solutions. It is critical to assure that the pH does not rise above 8.4 in order to avoid opening of the thiolactone ring (16), which would defeat the purpose of the previous step. Thus, the necessary volumes of NaOH are calibrated using a pH meter prior to each assay, in order to avoid day-to-day changes. Immediately following the pH adjustment, a concentrated solution of BSA (or 10 mM L-lysine) is added to the mixture in order to achieve a final concentration of 1 mM. The samples are placed on a rotating platform overnight in order to form homocystamide adducts. These solutions were used in a competitive antibody binding assays in parallel with "test solutions" that were analyzed for homocysteine concentrations.

Preparation of plasma specimens ("test solutions"). In experiments using homocysteine-spiked plasma, we sought to achieve a homocysteine-free ultrafiltrate of plasma prior to the addition of homocysteine. Plasma from a non-homocysteinemic individual was subjected to ultrafiltration, thereby removing the majority of endogenous homocysteine, which is bound to serum alubumin (107–109). The ultrafiltrate was spiked with known homocysteine concentrations. From this point on, the sample treatment was the same as described for the preparation of the standard solutions (above).

Immunoassay. 100 μl aliquots of competitor solutions and standards (above) were added to microtiter plates pre-coated with antigen. Subsequently, a limiting dilution of purified polyclonal antibody (100 μl) was added. The samples were incubated overnight and rinsed. A horseradish peroxidase-bound goat-anti-rabbit IgG secondary antibody was added and incubated for 2 hours. Following thorough washing of the plate, TMB was added. The reactions were quenched after 30 minutes by the addition of $H_2SO_4$ (1.8N) and read at 450 nm.

Data analysis. Sigma Plot 4.0 (Jandel Scientific) was used in order to fit a 4-parameter logistic function to the standard curve data, in order to obtain a concentration-dependent antibody binding profile for homocysteine. Concentrations of homocysteine in homocysteine-spiked plasma were determined using an assay transformation designed to be used with the 4-parameter logistic function and Sigma Plot 4.0.

Statistical significance was determined using Student's t-test.

4. Results

Figure 1B:
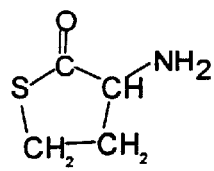
Figure 1B:
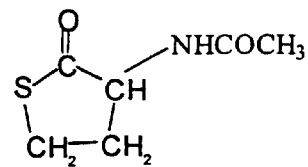
Figure 1B:
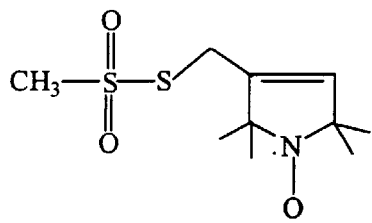
Figure 1B:
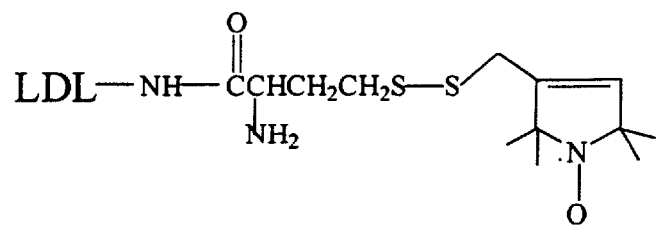
Figure 2:
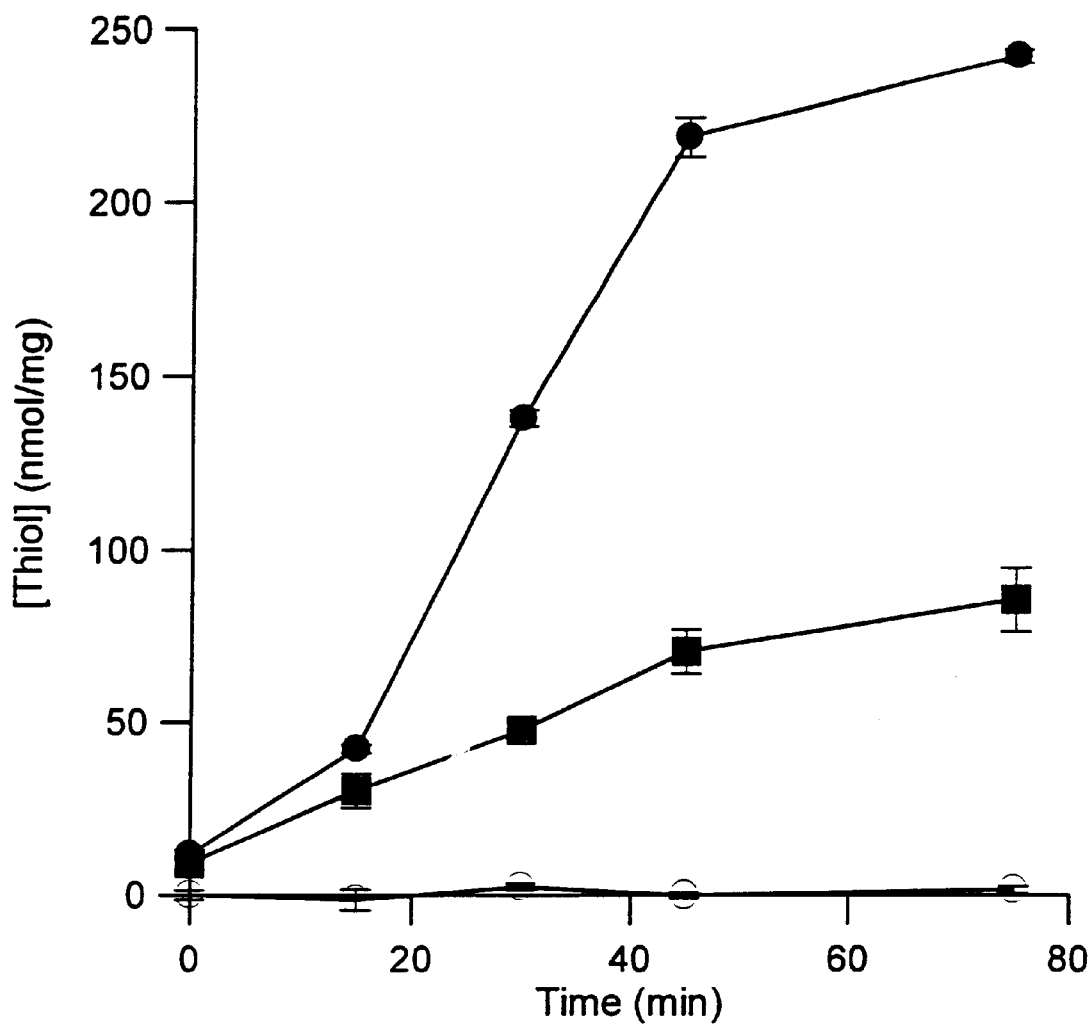
FIG. 2 charts the effect of homocysteine thiolactone, N-acetyl homocysteine thiolactone, and subsequent MTSL-treatment on LDL thiol concentrations as measured by the DTNB reagent. LDL (5 ml at 2.5 mg/ml) was incubated in PBS (pH 7.4, 100 μM DTPA) with homocysteine thiolactone free base freshly extracted from the hydrochloride salt (500 mg homocysteine thiolactone hydrochloride). At the indicated times, aliquots 0.75 ml aliquots were removed and passed through a Sephadex G-25 column. ●, Thiol concentrations were determined immediately using the DTNB reagent ($\epsilon$=11,000 M$^{-1}$ cm$^{-1}$). Subsequently, samples were incubated with MTSL (2.75 mM) overnight at 4° C. Samples were passed through a Sephadex G-25 column in order to remove unreacted MTSL. ○, Thiol concentrations were determined using the DTNB reagent. ■, Thiol concentrations in LDL treated with N-acetyl homocysteine thiolactone (see text for details). Values represent the mean±SEM.

Kinetics of thiol group generation in the reactions between homocysteine thiolactone versus N-acetyl-homocysteine thiolactone and LDL. The reaction between homocysteine thiolactone and apo-B lysyl residues was followed by measuring thiol concentrations. Homocysteine thiolactone free base was added to LDL (5 ml at 2.5 mg/ml in PBS containing DTPA 100 μM). FIG. 2 shows that incubation of LDL with homocysteine thiolactone resulted in a time-dependent increase in LDL-bound thiol content. Thiol concentrations increased over a 3 hour period and reached a maximum of 301±9 nmol per mg LDL at 3 hours. These data suggest that apo-B lysyl residues had become 83% acylated at 3 hours, indicated by the increase in thiol concentration (assuming 181 lysyl residues per apo-B molecule and a molecular weight of 500 kDa) (18). The reaction was not followed after 75 minutes, as the mixture had begun to aggregate and precipitate at that time. If homocysteine thiolactone is removed by gel filtration before the incubation time exceeds 75 minutes, aggregation does not take place. Following gel filtration in order to remove any unbound homocysteine thiolactone, mixtures containing LDL and homocysteine were treated with the thiol-blocking spin label, MTSL (FIG. 1B). The addition of MTSL completely blocked LDL-bound thiol groups, demonstrating the accessibility of thiol groups to hydrophilic thiol blockers (FIG. 2).

It has been suggested that homocysteine thiolactone is capable of intermolecular nucleophilic addition reactions (equation 5, FIG. 1A) (76). The N-acetylated derivative of homocysteine thiolactone, N-acetyl homocysteine thiolactone (FIG. 1B) prevents any nucleophilic reactions from occurring at the nitrogen atom. N-Acetyl-homocysteine thiolactone (500 mg) was incubated with LDL (5 ml at 2.5 mg/ml, DTPA 100 μM). At selected time intervals, aliquots were removed, and thiol concentrations were immediately determined. FIG. 2 shows that the increase in thiol content is slower in the reaction between N-acetyl-homocysteine thiolactone (FIG. 1B) and LDL than in the reaction between homocysteine thiolactone and LDL. It is possible that this difference exists because intermolecular nucleophilic addition reactions occur with homocysteine thiolactone, but not N-acetyl homocysteine-thiolactone. Therefore, individual lysyl residues of LDL incubated with homocysteine thiolactone may contain more than 1 molecule of homocysteine.

Locations of thiol groups in homocystamide-LDL adducts. ESR spin labeling has been used previously to characterize the locations of thiol groups in biological samples (92). FIG. 3A shows the ESR spectrum of native LDL in which the 5–6 endogenous thiol groups (cysteinyl residues) were labeled with MTSL. The spectrum is composite of two species. The major component consists of a rotationally restricted nitroxide (denoted ●). The minor component consists of a nitroxide with relatively fast rotational mobility (denoted ▲). In FIG. 3B, the water-soluble paramagnetic relaxing agent, CROX (100 mM), was added to the sample in 3A. Addition of CROX broadened out the fast tumbling nitroxide (denoted ▲) but did not affect the spectrum from the rotationally restricted nitroxide (denoted ●). This indicates that apo-B thiols lie in hydrophobic environments of LDL. This result is consistent with our previous report in which a similar spin label, MAL-6, was used to determine the locations of apo-B thiols (92). LDL was treated with homocysteine thiolactone for 75 minutes and subsequently with MTSL (FIG. 3C). In contrast to FIG. 3A, the spectral intensity in FIG. 3C is much higher due to an increased level of MTSL-labeling. FIG. 3C exhibits a narrow line-shape, indicating that the spin labels are rotating more freely in aqueous solution. This suggests that this population of spin labels is on the surface of LDL. To test this hypothesis, CROX (100 mM) was added to the sample in FIG. 3C. As shown in FIG. 3D, the ESR spectrum was broadened by the addition of CROX, indicating that a major fraction of the spin labels was exposed to CROX in the aqueous phase (FIG. 3C, ▼) A substantial percentage of spins (20% by double integration), however, is not accessible to the aqueous phase, as shown by the immobilized component (FIG. 3D, ■). These results are consistent with a reaction of homocysteine thiolactone with two populations of apo-B lysyl residues, a major portion exposed to an aqueous environment and a minor portion exposed to a hydrophobic environment (92).

Modification of homocysteine thiolactone-treated LDL. In order to compare the net charges of the homocysteine thiolactone-treated LDL with native LDL, samples were subjected to agarose gel electrophoresis. The REM of homocysteine thiolactone-treated LDL was increased for each of the thiolactone-treated samples (10 minutes homocysteine thiolactone-treated REM=1.49; 45 minute homocysteine thiolactone-treated REM=2.53), indicating an increase of net negative charge. This may be due to deprotonation of the thiol groups of homocystamide-LDL adduct, which is likely to occur, as the running buffer of the Paragon Lipo-Gel system is pH 8.9 (11). In these same samples, primary amino group concentrations were measured using the TNBS assay. The % TNBS-reactivity was 100±1.6 for native LDL, 105.1±4.7 for 10 minutes homocysteine thiolactone-treated LDL, and 104.6±5.0 for the 45 minute homocysteine thiolactone-treated LDL. These values are not significantly different (P>0.05, n=3 for each group). This observation is consistent with the proposed reaction (equation 2, FIG. 1A) in which the primary amino group concentration remains constant.

Figure 4:
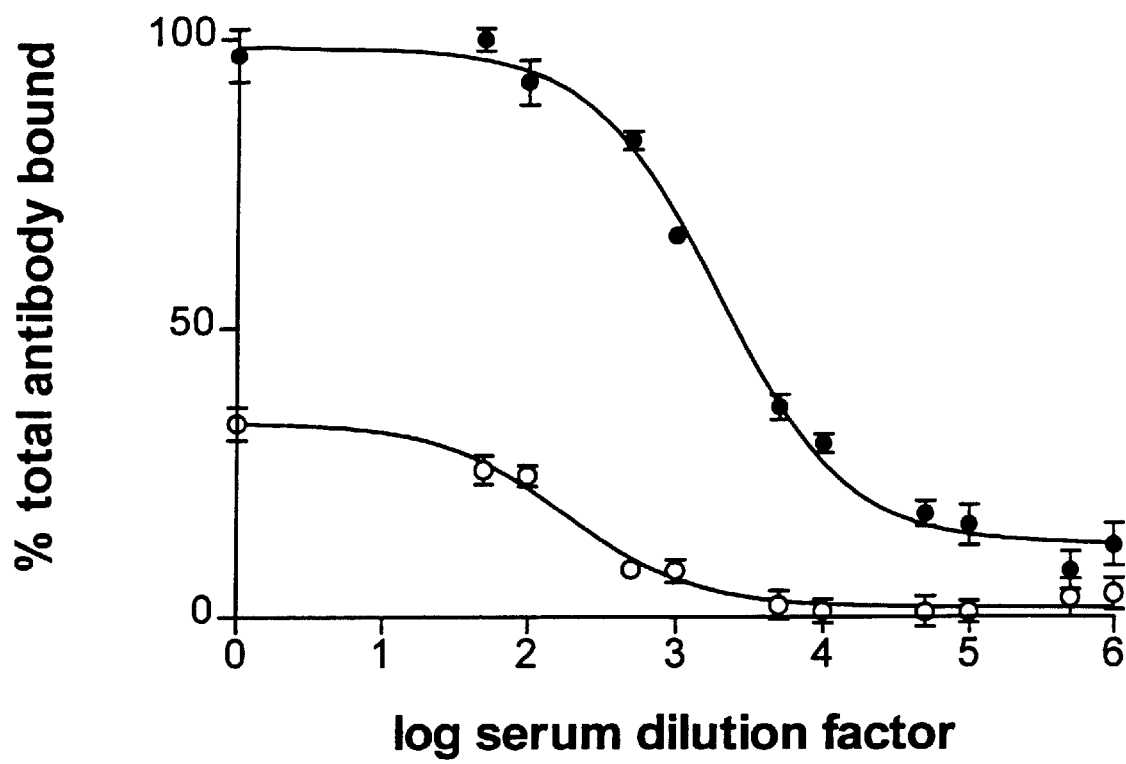
FIG. 4 is an antibody dilution curve for antiserum to rabbit homocystamide-LDL adduct. New Zealand White Rabbits were initially immunized with homologous homocystamide-LDL adduct (0.5 mg LDL, 30% lysinyl residues reacted with homocysteine thiolactone) emulsified in complete Freund's adjuvant. Later immunizations were spaced at 6-week intervals, but incomplete Freund's adjuvant was used in order to emulsify the LDL. Serum was collected 7 days following the third immunization. Serial dilutions of the antiserum were assayed by solid phase ELISA techniques in which LDL (100 μl, 10 μg/ml in PBS) was bound to Millipore 96-well plates. Horseradish peroxidase-labeled goat-anti-rabbit IgG was used as a secondary antibody, and TMB was used as a substrate. ●, Immune serum following the third immunization. ○, Pre-immune serum. (n=3 for each data point. Values are the mean±SEM).

Determination of Antibody Titers. Prior to immunization procedures, pre-immune sera were obtained from two New Zealand white rabbits in order to determine nonspecific binding in future assays. Rabbits were immunized as described in the Materials and Methods section. Seven days following the second immunization, blood was collected from the animals, and serum was obtained. The antiserum and the pre-immune serum from each animal was assayed for antibody titers. Homocysteine thiolactone-treated rabbit LDL (10 µg/ml) was coated onto 96 well plates. After blocking with BSA and washing, antiserum (1:10–1:10$^6$) was added. Antibody binding was measured as described above. Titers from this immunization were approximately 10$^5$ (titers defined in Materials and Methods section). Binding of the pre-immune serum was non-existent. Human LDL was used in the remaining assays reported here, as titers were the same when using either rabbit LDL or human LDL. The immune responses of both rabbits following the third immunization roughly mirrored the second immunization. As shown in FIG. 4, antibody titers 7 days following the third immunization were approximately 10$^5$ (serum dilution curve shown from 1 animal only). Maximum binding was reached at an antiserum dilution of 1:100, as the percentage of the total antibody bound was not significantly different (p>0.05) in less dilute samples (FIG. 4).

We sought to determine whether or not homocystamide adducts of other proteins could also be used in order to measure antibody titers. Both hemoglobin and BSA were treated with homocysteine thiolactone, as described in the Materials and Methods section. Solid phase ELISA techniques, as described for FIG. 4 were used in order to obtain a serum dilution curve for homocystamide-BSA adduct and for homocytamide-hemoglobin adduct. This curve resembled the serum dilution curve obtained in FIG. 4, as the antiserum recognized both homocystamide-BSA and homocystamide-hemoglogin adduct, indicated by antiserum dilution-dependent increase in the absorbance at 450 nm. Neither native BSA nor native hemoglobin were recognized by the antiserum (n=2 for each measurement).

Figure 3:
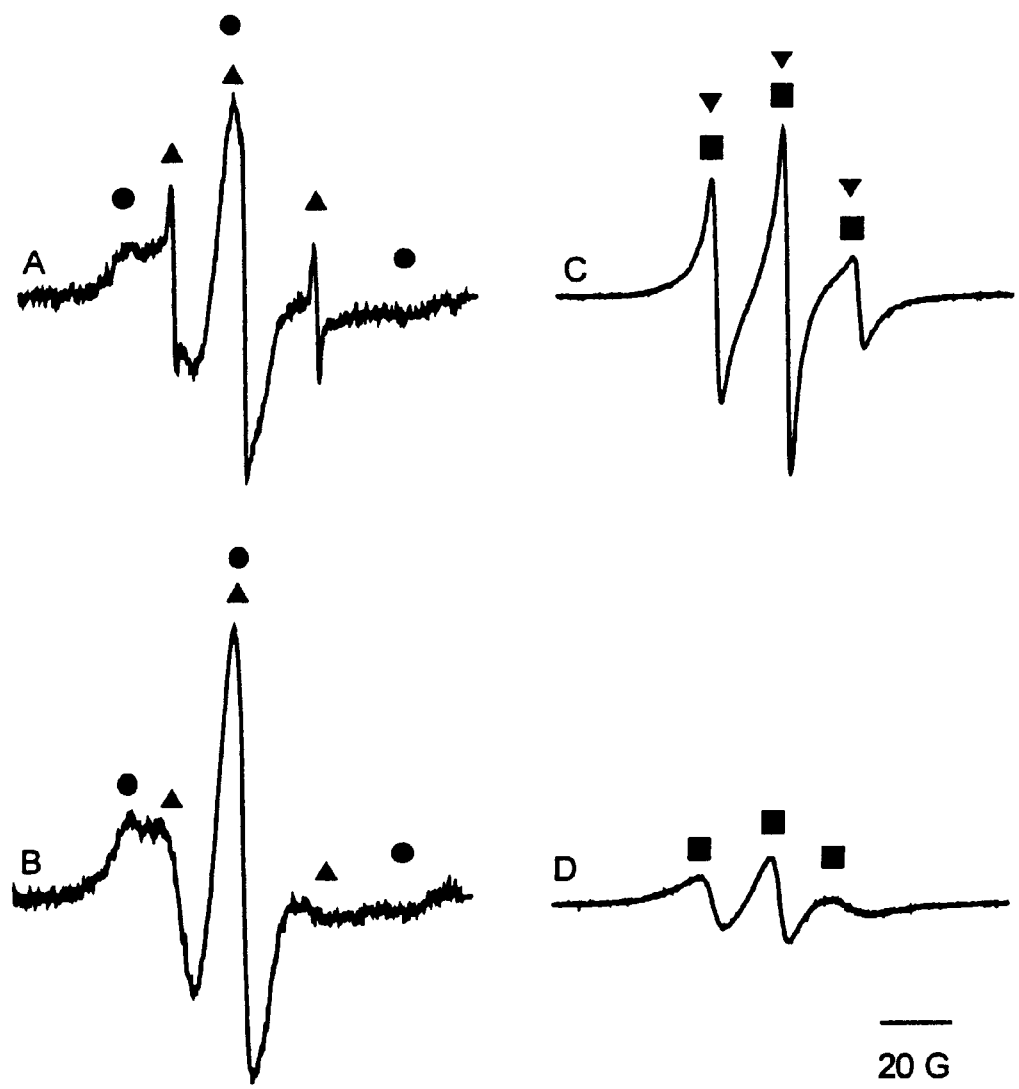
FIGS. 3A, B, C and D are ESR spectra of spin-labeled MTSL-modified homocystamide-LDL adduct.
FIG. 3C is MTSL-labeled homocystamide-LDL adduct.
FIG. 3B and D are the same as FIGS. 3A and C but in the presence of CROX (100 mM). ▲ and ● represent the mobilized and immobilized components of the MTSL-LDL spin adduct, respectively. ▼ and ■ represent the mobilized and immobilized components of the MTSL-homocystyamide-LDL spin adduct, respectively. ESR conditions: scan range, 100 G; field setting, 3368 G; time constant, 0.128s$^{-1}$; modulation amplitude, 1 G; microwave power, 5 mW; gain, 2.5×10$^5$ (a and b), 1.6×10$^4$ (c and d).
Figure 5:
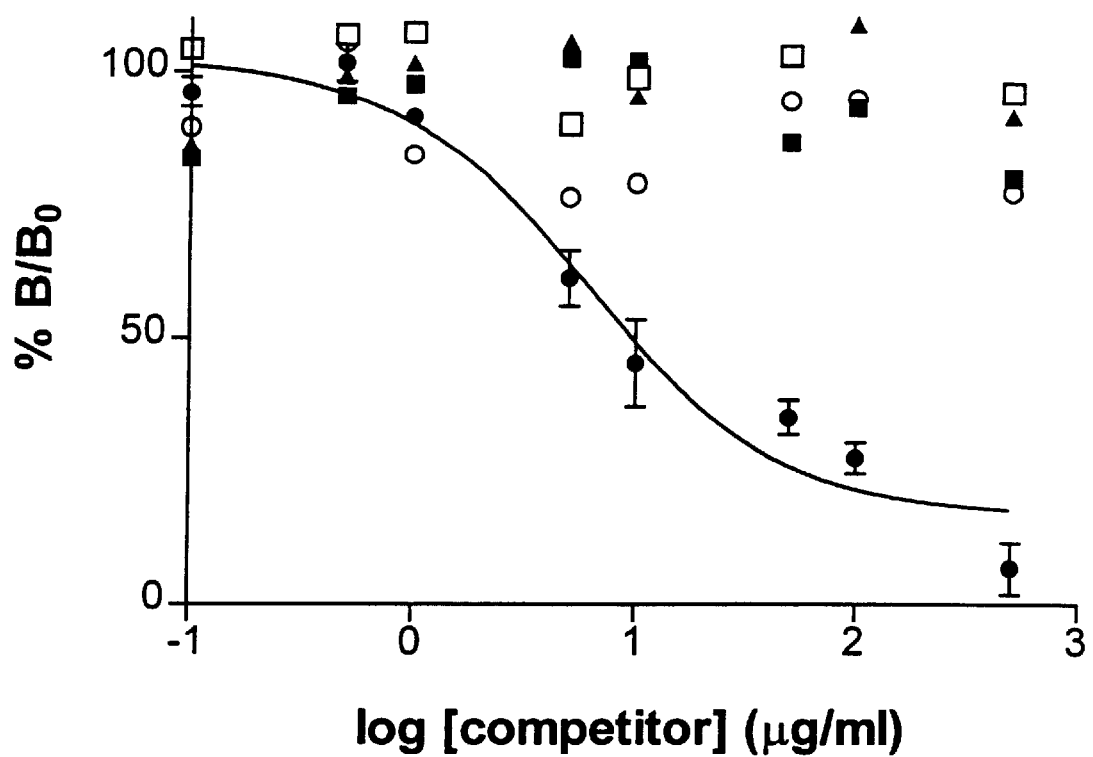
FIG. 5 demonstrates the specificity of antiserum to homocystamide-LDL adduct with respect to various lysine modifications. Antiserum obtained as described in FIG. 1 was added to Millipore 96-well plates containing pre-adsorbed homocystamide-LDL adduct (100 μl, 10 μg/ml) at a limiting dilution (1:700) in the indicated concentrations of competitors (●, homocystamide-LDL adduct, ○, native LDL, □, acetylated LDL, ▲, methylated LDL, ■, methylated LDL treated with homocysteine thiolactone). Following a 12 hour incubation, antibody bound was quantified as described in FIG. 2. Results are presented as %B/B$_0$, in which B is the amount of antibody bound in the presence of a given concentration of competitor and B$_0$ is the amount bound in the absence of competitor. This experiment is representative of 3 independent experiments. (n=3 for each data point. Data points are the mean±SEM).

Antigenicity of Modified LDL Lysyl Residues. We sought to examine the specificity of the antiserum with respect to various lysine modifications, including the immunization compound, the homocystamide-LDL adduct. Homocysteine thiolactone-treated LDL (10 µg/ml) was coated onto 96-well plates. As shown in FIG. 5, after blocking with BSA and washing the plates, homocystamide-LDL adduct (0.01–500 µg/ml) was added to the wells in the presence of a constant limiting dilution (1:700) determined from FIG. 4. As shown in FIG. 5, a dose-dependent inhibition of antiserum binding to the solid phase was observed for the homocystamide-LDL adduct. The concentration of homocystamide-LDL adduct which was required to cause a 50% decrease of %B/B$_0$ (IC$_{50}$) (in which B$_0$ was defined as the total binding in the absence of competitor and B was total binding in the presence of competitor) was approximately 10 µg/ml (FIG. 5). Native LDL did not compete for binding, as a dose-dependent decrease in %B/B$_0$ was not observed (FIG. 3). Similarly, neither BSA nor homocysteine disulfide (homocystine) were recognized, as a dose-dependent decrease in %B/B$_0$ was not observed. In order to determine whether the antibody was directed against homocystamide-LDL adduct or derivatized lysine in general, LDL was acetylated, as described in Materials and Methods. Acetylation was assessed qualitatively by measuring REM, as described in Materials and Methods. The REM of acetylated LDL was 6.13±0.04 (n=3). When acetylated LDL was used as a competitor, a dose-dependent decrease in %B/B$_0$ was not observed, which provided further evidence that the antiserum was specific for the homocystamide-LDL adduct (FIG. 5). In order to determine whether the antigenicity of homocystamide-LDL adduct was due to the adduct itself or conformational changes in apo-B induced by homocysteine thiolactone, LDL was reductively methylated. A 93±4% decrease in apo-B lysyl residues was observed, as measured by the TNBS assay (assuming 180 lysines per apo-B, and a 500,000 molecular weight, n=3 for each measurement). A portion of the methylated LDL was treated with homocysteine thiolactone using identical conditions to the formation of homocystamide-LDL adducts. Neither methylated LDL nor homocysteine thiolactone-treated methylated LDL competed for binding (FIG. 5). (This experiment is representative of 3 independent experiments. n=3 for each measurement). This demonstrates that the antigenicity of homocystamide-LDL adduct is due to direct effects of homocysteine thiolactone on lysyl residues and not due to nonspecific modifications of LDL by homocysteine thiolactone.

Figure 6:
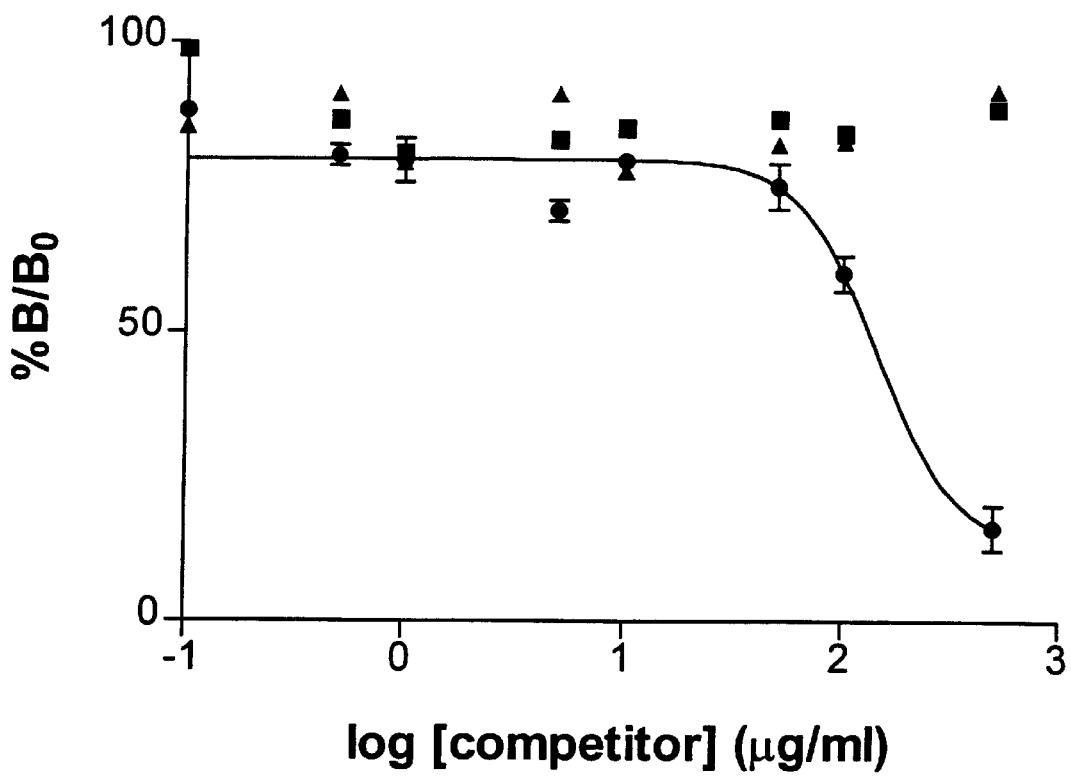
FIG. 6 demonstrates the specificity of antiserum to homocystamide-LDL adduct following Cu$^{2+}$-mediated oxidation. Antiserum obtained as described in FIG. 1 was added to Millipore 96-well plates containing pre-adsorbed homocystamide-LDL adduct (100 μl, 10 μg/ml) at a limiting dilution (1:700) in the indicated concentrations of competitors (●, Cu$^{2+}$-oxidized homocystamide-LDL adduct, ■, Cu$^{2+}$-oxidized LDL, ▲, homocysteine). Following a 12 hour incubation, antibody bound was quantified as described in FIG. 1. Results are presented as %B/B$_0$, in which B is the amount of antibody bound in the presence of a given concentration of competitor and B$_0$ is the amount bound in the absence of competitor. This experiment is representative of 3 independent experiments. (n=3 for each data point. Data points are the mean±SEM).

The specificity of the antiserum for the homocystamide-LDL adduct was investigated further by examining the effect of Cu$^{2+}$-mediated LDL oxidation on its antigenicity. Homocystamide-LDL adduct was prepared as described in FIG. 5. Homocystamide-LDL adduct (0.5 mg/ml) and native LDL (0.5 mg/ml) were dialyzed in EDTA-free, Chelex-treated PBS for 24 hours. Following dialysis, Cu$^{2+}$ (100 µM) was added to each of the samples, which were incubated at 37° C. for 6 hours. Following incubation, BHT (500 µM) and EDTA (1 mM) were added to quench the reactions. TBARS were measured at this time, as described in Materials and Methods. TBARS concentrations were 68.4±0.5 nmol/mg in homocysteine thiolactone-treated LDL and 62.1±0.2 nmol/mg in native LDL (n=3 for each measurement). As in FIG. 5, competition assays were performed in order to determine specificity of the antiserum for the above modifications. As shown in FIG. 6, homocysteine thiolactone-treated LDL which was oxidized with Cu$^{2+}$ competed for binding in a dose-dependent manner, with an IC$_{50}$ of approximately 100 µg/ml. This level of competition is less than for the homocystamide-LDL adduct (IC$_{50}$=10 µg/ml) (FIG. 5). Two possibilities could explain this observation. First, the oxidized product could be a less potent competitor. Second, this extent of Cu$^{2+}$ oxidation could have incompletely destroyed the antigens on homocysteine thiolacone-treated LDL. Cu$^{2+}$-oxidized LDL which was not pre-treated with homocysteine thiolactone did not compete (FIG. 6). Also, free homocysteine was tested as a competitor and did not compete for binding (FIG. 6).

Figure 7:
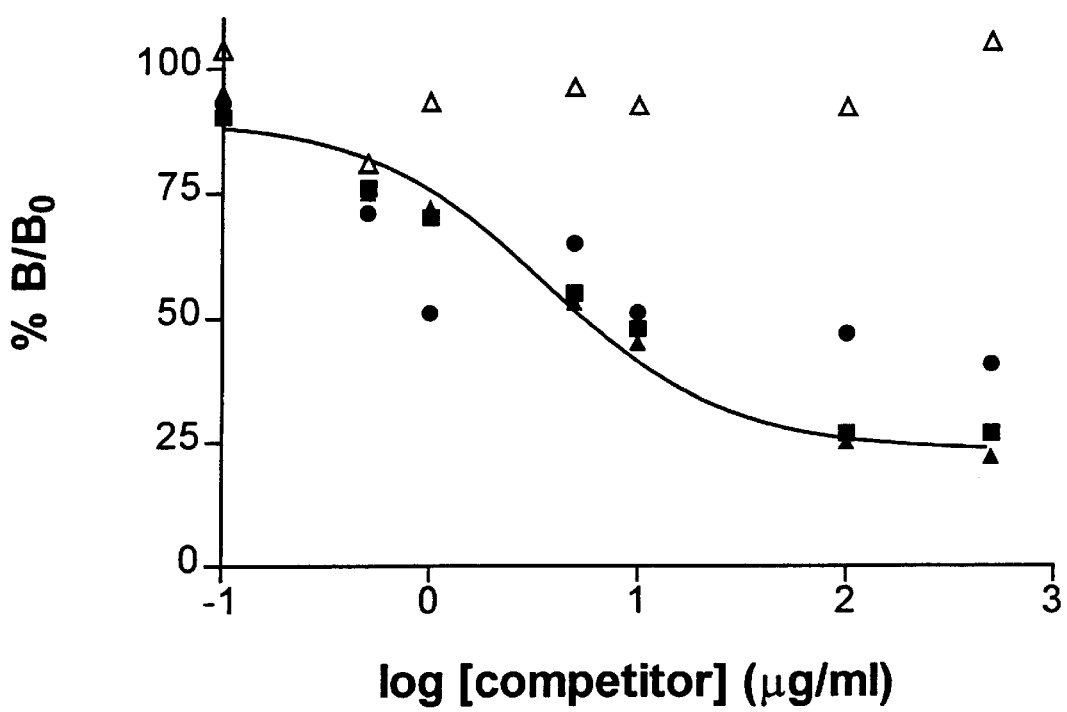
FIG. 7 shows the identification of specific homocystamide-adducts in homocysteine thiolactone-treated plasma. Antiserum obtained as described in FIG. 1 was added to Millipore 96-well plates containing pre-adsorbed homocystamide-LDL adduct (100 μl, 10 μg/ml) at a limiting dilution (1:700) in the indicated concentrations of competitors (▲, ●, ■, homocystamide-LDL, -HDL, and -lipoprotein-deficient serum proteins isolated from homocysteine thiolactone-treated plasma, and freshly drawn plasma without homocysteine thiolactone treatment, Δ). Following a 12 hour incubation, antibody bound following a 2-hour incubation, antibody bound was quantified as described in FIG. 1 using horseradish peroxidase-linked goat-anti-rabbit IgG (heavy and light chains). Results are presented as %B/B$_0$, in which B is the amount of antibody bound in the presence of a given concentration of competitor and B$_0$ is the amount bound in the absence of competitor. (n=4 for each data point. Data points are the mean±SEM). Results are presented as %B/B$_0$, in which B is the amount of antibody bound in the presence of a given concentration of competitor and B$_0$ is the amount bound in the absence of competitor. (This experiment is representative of 3 independent experiments. Data points are the mean of duplicate measurements.)

Antigenicity of Homocysteine Thiolactone-Treated Plasma. In order to determine whether protein homocystamide-lysyl adducts could be detected in plasma proteins, freshly drawn human plasma was treated with homocysteine thiolactone and compared to native plasma. The plasma solution was added to homocysteine thiolactone free base (500 mg). This solution was incubated 30 minutes on ice with gentle stirring and was passed through a Sephadex G-25 column in order to remove unreacted homocysteine thiolactone. Subsequently, LDL, HDL, and LPDS were isolated by sequential ultracentrifugation in a potassium bromide gradient. The presence of homocystamide-lysine adducts was determined by using competition assays. As shown in FIG. 7, protein homocystamide-lysine adducts were present in LDL, HDL, and in the LPDS fractions of the homocysteine thiolactone-treated plasma, as indicated by their dose-dependent inhibitory effects. In contrast, inhibition was not observed for untreated plasma (FIG. 7). Neither of the 3 fractions (LDL, HDL, LPDS) isolated from untreated plasma showed an inhibitory effect.

Figure 8:
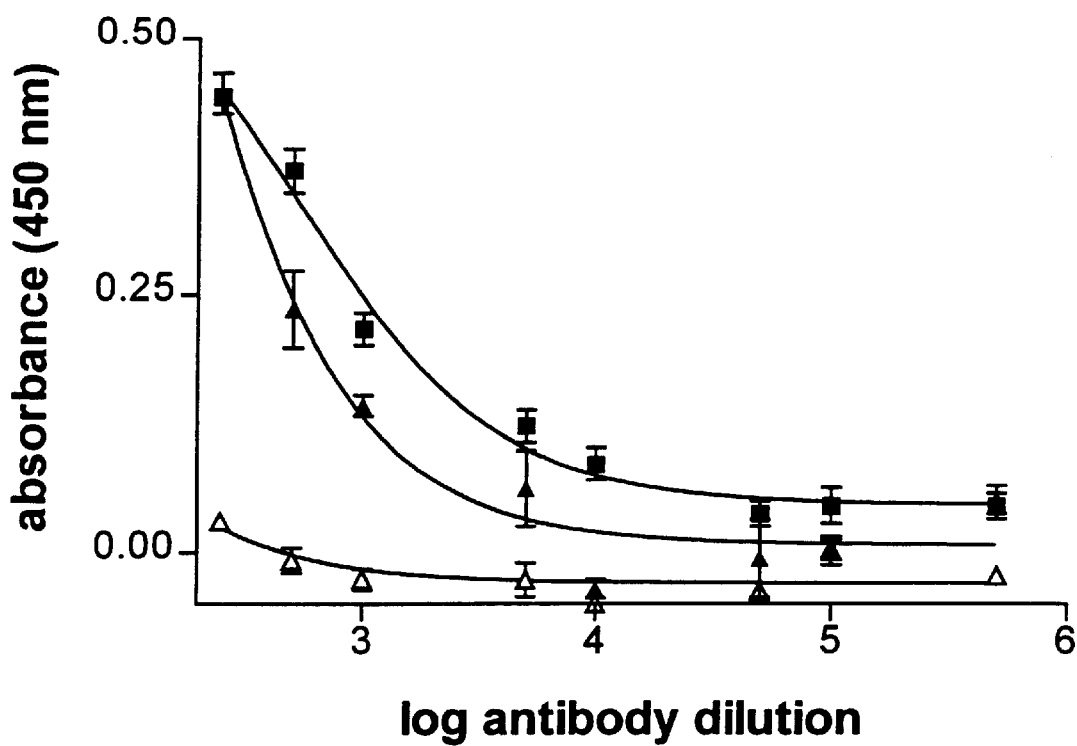
FIG. 8 is an antibody dilution curve and immunoglobulin class for purified polyclonal antibody directed against the homocystamide adduct. Antiserum directed against the homocystamide adduct was obtained from New Zealand White Rabbits. Following an initial ammonium sulfate precipitation, the antibody of interest was purified using an antigen column consisting of homocysteine-bound aminohexylsepharose. Protein concentration of the antibody solution was 0.55 mg/ml. Serial dilutions of the antibody were assayed by solid phase ELISA techniques in which homocystamide-LDL adduct and untreated LDL (100 μl, 10 μg/ml in PBS) were bound to 96-well polystyrene plates. Horseradish peroxidase-labeled goat-anti-rabbit IgG (heavy and light chains, ■), anti-rabbit IgG (F$_c$, ▲), and anti-rabbit IgM (μ chain, Δ) were used as a secondary antibodies. TMB was used as a substrate. Results represent the difference in absorbance between homocystamide-LDL adduct and untreated LDL. (n=3 for each data point. Values are the mean±SEM).

Purification and characterization of the polyclonal antibody. The polyclonal antiserum was purified using an antigen column, as described in materials and methods. We sought to determine antibody class of the purified antibody. FIG. 8 indicates that only IgG is present in appreciable quantities, as shown by the increased absorbances for both the heavy chain-specific and the heavy and light chain-specific secondary antibodies. IgM was present in very minor proportions, as shown by the low absorbance at all dilutions for the $\mu$-chain-specific secondary antibody. Results are the difference in absorbance between binding to homocystamide-LDL and native LDL. (n=4 for each data point). Heavy and light chain-specific secondary antibodies were used in all remaining experiments. A limiting dilution (1:300) if of primary antibody was determined from this experiment and was used in all competition ELISAs.

We sought to determine the specificity of the purified polyclonal antibody toward the homocystamide-LDL adduct. Homocystamide-LDL (100 $\mu$l, 10 $\mu$g/ml) was bound to the solid phase of 96-well ELISA plates. Homocystamide-LDL competed for binding to the solid phase with and $IC_{50}$ of 15 $\mu$g (95% confidence interval 6–39 $\mu$g) Neither native LDL nor LDL in which the lysyl residues were acetylated competed for binding (n=4 for each data point). This demonstrates that the purified antibody is directed against the homocystamide-LDL adduct and not lysyl residue modifications in general.

The specificity of the purified polyclonal antibody toward other non-homocystamide adduct molecules was investigated. Homocystine (homocysteine disulfide) was solubilized in 1N sodium hydroxide, and the pH was slowly dropped to 7.4 using concentrated hydrochloric acid. Homoserine lactone-treated and N-acetyl homocysteine thiolactone-treated LDL were also obtained. The extent of LDL modification was evaluated qualitatively by agarose gel electrophoresis. The REM of homoseramide-LDL adduct and N-acetyl-homocystamide LDL adduct was 1.5 and 1.4, respectively. Homocystine competed for antibody binding to the solid phase with an $IC_{50}$ of 68 $\mu$g (95% confidence interval 32–147 $\mu$g). Neither homoseramide-LDL adduct nor N-acetyl homocystamide-LDL adduct were recognized by the purified polyclonal antibody. This further demonstrates the specificity of the antibody, as the homocysteine structure is necessary and sufficient for recognition.

In order to investigate the versatility of the purified polyclonal antibody, homocystamide adducts were prepared on BSA, KLH, and hemoglobin in order to perform competition ELISAs. BSA competed for binding to the solid phase (homocystamide-LDL adduct) with an $IC_{50}$ of 15 $\mu$g (95% confidence interval 2–17 $\mu$g). Untreated BSA was not recognized (n=4 for each data point). KLH and hemoglobin competed for binding to the solid phase (homocystamide-LDL adduct) with an $IC_{50}$ of 6 $\mu$g (95% confidence interval 2–17 $\mu$g) and 8 $\mu$g (95% confidence interval 4–17 $\mu$g), respectively. Untreated KLH and hemoglobin were not recognized. These data demonstrate that the purified polyclonal antibody is not protein-specific, as the homocystamide adduct on proteins other than LDL are recognized.

Native LDL and homocystamide-LDL were subjected to SDS PAGE. Myosin (M.W. 204 kDa) was used as a molecular weight standard. In parallel, an identical gel was subjected to electrophoresis and subsequently, Western blotting. The purified polyclonal antibody recognized the homocystamide-LDL but not native LDL nor myosin. This experiment demonstrates that the homocystamide adduct was bound to LDL and that the homocystamide-LDL adduct retained its antigenicity following denaturing.

We sought to determine whether homocystamide adducts of other proteins could be identified using Western blotting techniques. Homocystamide-KLH and untreated KLH were subjected to SDS PAGE. Multiple bands were observed in both lanes, consistent with the dissociation of KLH in solution. In parallel, an identical gel was subjected to electrophoresis for Western blotting. The homocystamide-KLH adduct but not untreated KLH was detected. A similar experiment was performed with homocystamide-BSA adduct and untreated BSA. Following SDS PAGE, a major band was observed that represented BSA [minor bands represent impurities in the commercially available BSA ($\geq$98% pure)]. Using Western blotting techniques, the homocystamide-BSA adduct but not untreated BSA was detected. These experiments demonstrate that the purified polyclonal antibody recognizes homocystamide adducts on proteins other than homocystamide-LDL adduct.

Antibody affinity for D,L- versus L-homocystamide adduct. D,L Homocysteine thiolactone or L-homocysteine thiolactone (50 mM) was incubated with BSA (1 mg/ml) for 6 hours at 25° C. on a rotating platform. Following incubation, the solutions were de-salted using Sephadex G-25 columns. Homocystamide-BSA adducts (0–500 $\mu$g/ml) were employed as competitor solutions in a competition-based ELISA, as in FIG. 4. A similar concentration-dependent antibody binding profile was observed for both D,L and L-homocystamide-BSA, as the $IC_{50}$ values for both samples were not significantly different (P>0.05) (data not shown). These observations suggest that the antibody affinity for D- versus L-homocystamide-BSA adduct is the same.

Utility of the Present Polyclonal Antibody to Detect Homocysteine

HCl-catalyzed Dehydration of Homocysteine. The HCl-catalyzed formation of homocysteine thiolactone was investigated. Homocysteine (75 $\mu$M) was incubated at 25° C. in the presence of HCl (6N) and DTT (1 mM). DTPA (100 $\mu$M) was included in order to prevent adventitious metal ion-catalyzed oxidation. The absorbance was followed for several hours. As shown in FIG. 9A, maxima at 240 nm, reflecting formation of homocysteine thiolactone, occur. The effect of raising the temperature was investigated. As shown in FIG. 9B, the dehydration of homocysteine to homocysteine thiolactone occurs much more rapidly at 60° C., as conversion is nearly complete within 2 hours. These data indicate that homocysteine can be easily converted to homocysteine thiolactone.

The efficiency of the HCl-mediated conversion of homocysteine to homocysteine thiolactone was investigated for various concentrations of homocysteine. Homocysteine was incubated at the indicated concentrations (Table 1) for 2 hours at 60° C. in the presence of DTT (1 mM), DTPA (100 $\mu$M), and HCl (6N). Samples were collected, and the absorbance at 240 nm was measured. As indicated in Table 1, these conditions are adequate for quantitative conversion of homocysteine to homocysteine thiolactone.

TABLE 1

Efficiency of HCL-mediated homocysteine conversion to homocysteine thiolactone.

| [homocysteine] ($\mu$M) | [thiolactone] formed ($\mu$M) | SEM | % conversion |
|---|---|---|---|
| 5 | 5.1 | 1.0 | 102.0 |
| 10 | 10.2 | 0.5 | 101.6 |
| 25 | 23.9 | 0.6 | 95.6 |

TABLE 1-continued

Efficiency of HCL-mediated homocysteine conversion to homocysteine thiolactone.

| [homocysteine] ($\mu$M) | [thiolactone] formed ($\mu$M) | SEM | % conversion |
|---|---|---|---|
| 50 | 49.1 | 1.1 | 98.2 |
| 75 | 75.3 | 1.5 | 100.4 |

Effect of plasma on the HCl-catalyzed dehydration of homocysteine. Normal human plasma was obtained and spiked with a concentrated solution of homocysteine (final concentration 75 $\mu$M in 1.0 ml). DTPA (100 $\mu$M), EDTA (1 mM), and perchloric acid (0.6 mM) were added, and the sample was centrifuged for 5 minutes at 3500 g. The supernatant was transferred into a clean tube. HCl (6N) was added, and the mixture was incubated for 2 hours at 60° C. Following the incubation, the volume was raised to 1.0 ml with $H_2O$, and the absorbance (minus a blank consisting of the above mixture in the absence of homocysteine) was measured in a quartz cuvette. Homocysteine thiolactone was recovered quantitatively by this procedure (>95% efficiency), although it would be challenging to use this method for measuring physiological concentrations of homocysteine due to high background absorbancy in the ultraviolet region of the reducing agents that are required for the measurement of total plasma homocysteine.

Figure 10:
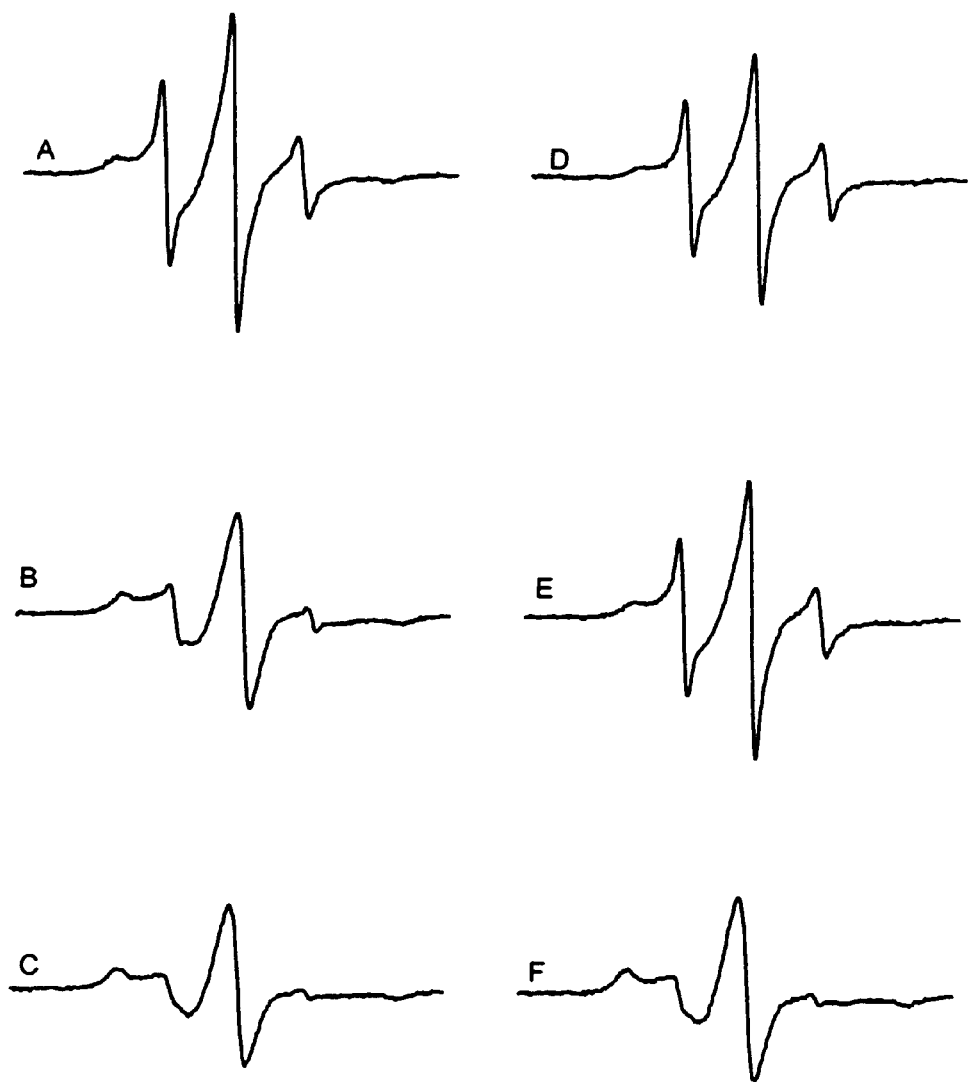
FIGS. 10A–F demonstrates homocysteine coupling to BSA as measured by the thiol-reactive spin label MTSL and ESR. BSA (200 μM in 1 M borate buffer, pH 8.4, DTPA 100 AM) was incubated for 3 hours in the presence of homocysteine thiolactone (2 mM), homocysteine (2 mM), or PBS (FIGS. 10A–C, respectively). Following incubation, samples were desalted using Sephadex G-25 columns, and MTSL (2 mM) was added. After an additional 1 hour incubation, excess MTSL was removed by Sephadex G-25 columns. Protein concentrations were determined, and samples were adjusted so that the BSA concentration was 150 μM. ESR spectra were recorded.

Coupling of homocysteine thiolactone to BSA. BSA (200 $\mu$M in 1 M borate buffer, pH 8.4, DTPA 100 $\mu$M) was incubated for 3 hours in the presence of homocysteine thiolactone (2 mM), homocysteine (2 mM), or PBS. Following incubation, samples were desalted using Sephadex G-25 columns, and MTSL (2 mM) was added. After an additional 1 hour incubation, excess MTSL was removed by Sephadex G-25 columns. Protein concentrations were determined, and samples were adjusted so that the BSA concentration was 150 $\mu$M. ESR spectra were recorded. As shown in FIG. 10C, the ESR spectrum for spin labeled native BSA is characteristic of a rotationally restricted nitroxide indicating that the thiols lie in non-aqueous environments. Spin labeled homocysteine thiolactone-treated BSA is shown in FIG. 10A. The ESR spectrum has 2 components, an immobile component arising from the spectrum of native BSA, and a mobile component corresponding to MTSL bound to homocystamide-lysine adduct on the surface of BSA. The effect of pre-incubating BSA with homocysteine on the resulting ESR spectrum is shown in FIG. 10B, which is nearly identical to that of native BSA (FIG. 10C). If however, homocysteine is pre-treated with 6N HCl, heated for 2 hours at 60° C., and neutralized to pH 8.4 prior to incubation with BSA, a spectrum similar to FIG. 10A is obtained (FIG. 10E). This indicates that homocysteine was bound to BSA by the intermediate formation of homocysteine thiolactone.

The effect of the water-soluble paramagnetic relaxing agent, CROX (50 mM) on the ESR spectra was determined. CROX broadened the mobile component of the ESR spectra described above, demonstrating that the homocystamide adduct is exposed to the aqueous phase. This is analogous to the locations of homocystamide adducts of LDL (FIGS. 3C, 3D).

Determination of antibody titers. In order to determine correct limiting dilutions of antibody to be used for competition ELISA, purified polyclonal anti-homocystamide adduct antibody was diluted, and added to antigen pre-coated plates, as described in Materials and Methods. Following a 2 hour incubation, a horseradish peroxidase-linked secondary antibody used in order to detect antibody binding. An antibody dilution of 1:400 was used for all remaining ELISAs, as this concentration is sub-maximal.

Determination of antibody specificity. Antibody specificity for homocystamide-BSA adduct was determined. Indicated concentrations of homocystamide-BSA adduct were added to antigen-coated plates. A limiting dilution of primary antibody (diluted in BSA (1%)) was added. Results of antibody binding are expressed as $B/B_0$, in which B is the % antibody binding in the presence of competitor, and $B_0$ is the % antibody binding in the absence of competitor. Homocystamide-BSA inhibited antibody binding with an $IC_{50}$ of approximately 200 $\mu$g/ml. Competition by native BSA was non-existent. These data demonstrate the specificity of the purified polyclonal antibody for the homocystamide-BSA adduct.

Determination of homocysteine concentrations using ELISA. We sought to determine whether our antibody could be used to measure homocysteine concentrations based on the HCl-mediated conversion of homocysteine to the corresponding thiolactone, subsequent neutralization and incubation with BSA, and detection of the acylated product. Standard solutions of homocysteine were prepared and converted to homocysteine thiolactone, and subsequently incubated with BSA as described in Materials and Methods. The resulting incubations were used as competitor solutions in an ELISA. Results indicate that homocysteine concentrations ranging from 5–100 $\mu$M can be determined using this method.

Plasma was obtained from a fasting healthy human volunteer. Free plasma homocysteine was non-existent, as determined by HPLC. The failure to observe homocysteine in plasma is easily explained by the omission of reductant in the sample pre-treatment (see Materials and Methods). In order to obtain relatively protein-free and homocysteine-free plasma, plasma was treated as described in Materials and Methods. In addition, a reducing agent was not employed in order to eliminate the possibility of any remaining low-molecular weight disulfides of homocysteine contributing to the assay.

Effect of plasma on ELISA detection of homocysteine. Aliquots of the treated plasma were separated and spiked with known concentrations of homocysteine (Table 2). The resulting solutions were treated such that endogenous homocysteine would be converted into homocysteine thiolactone and coupled to BSA, as described in Materials and Methods. Homocysteine concentrations were calculated in 3 experiments (Table 2). Results indicate that homocysteine can be estimated in human plasma with the indicated accuracy and precision in the concentration range of 25–100 $\mu$M (Table 2). By these principles, it is possible to detect homocysteine in plasma using the newly discovered antibody.

TABLE 2

Effect of plasma on the determination of homocysteine by ELISA using BSA as a carrier molecule.

| Homocysteine ($\mu$M) amount added | Homocysteine ($\mu$M) (ELISA) | SEM | % Recovery |
|---|---|---|---|
| 5 | 12.4 | 2.9 | n.d. |
| 25 | 27.5 | 13.5 | 110 |
| 50 | 62.1 | 12.9 | 124 |

TABLE 2-continued

Effect of plasma on the determination of
homocysteine by ELISA using BSA as a carrier molecule.

| Homocysteine (μM) amount added | Homocysteine (μM) (ELISA) | SEM | % Recovery |
|---|---|---|---|
| 75 | 80.3 | 7.6 | 107 |
| 100 | 95.1 | 5.2 | 95.1 |

Figure 11:
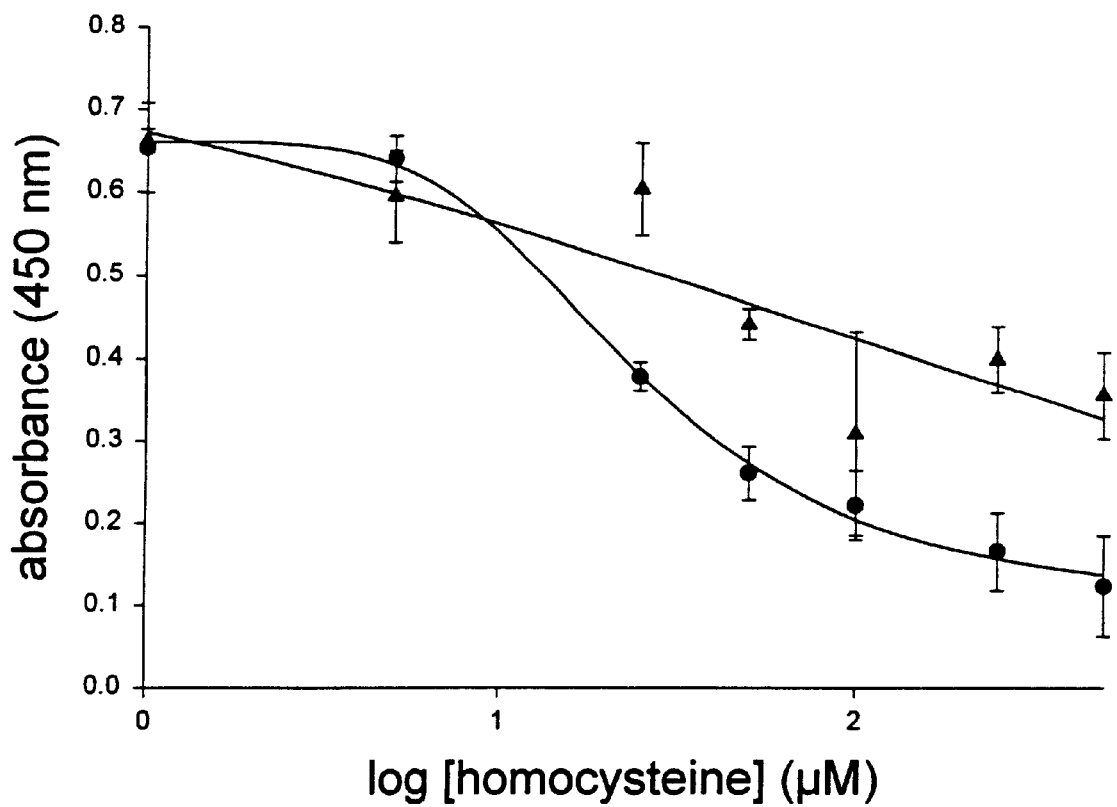
FIG. 11 demonstrates the determination of homocysteine concentration by ELISA using gylycylglycylglycine and L-arg as carrier molecules. A standard curve using authentic homocyteine was prepared as described in Materials and Methods using either gylycylglycylglycine (●) or L-arginine (▲) as a carrier molecule for the homocystamide adduct and ELISA. (n=3 for each data point).
Figure 12:
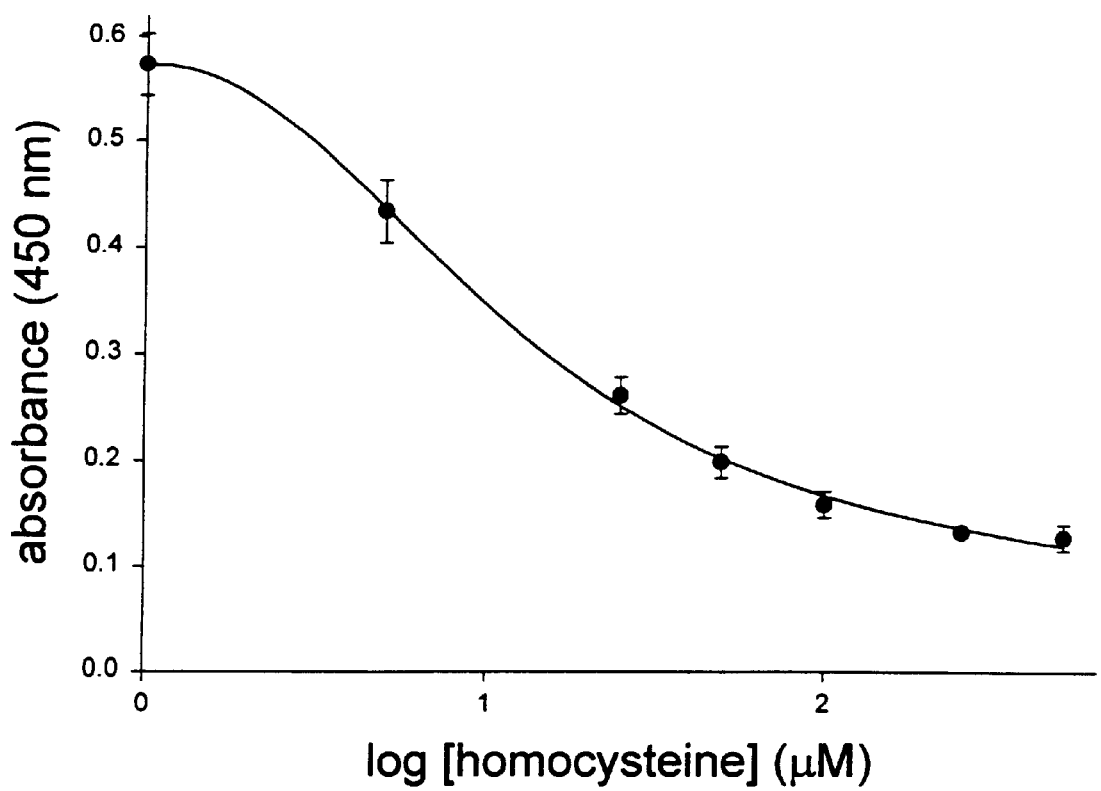
FIG. 12 demonstrates the determination of homocysteine concentration by ELISA using L-lysine as a carrier molecule. A standard curve using authentic homocyteine was prepared as described in Materials and Methods using L-lysine (●) as a carrier molecule and ELISA. (This experiment is representative of 3 independent experiments).

We sought to determine whether carrier molecules other than BSA could be employed for this assay, as it is possible that the sensitivity and precision could be improved. Homocysteine (0–500 μM) was measured by ELISA, except that different carrier molecules were employed. As shown in FIG. 11, glycylglycylglycine was employed. Using the tripeptide, which contains a single primary amine, a homocysteine concentration-dependent antibody-binding profile was observed. Using L-arginine in an analogous manner, however, yielded a poor antibody-binding profile, as homocysteine-arginine adducts weakly inhibited antibody binding (FIG. 11). In the same manner, polylysine yielded equally poor results (data not shown). As shown in FIG. 12, L-lysine proved to be an effective carrier molecule, as a useful range of homocysteine concentrations (~5–150 μM) could be determined in homocysteine-spiked human plasma samples using the logistic function that was used to fit these data (Table 3).

TABLE 3

Effect of plasma on the determination of
homocysteine by ELISA using L-lysine as a carrier
molecule.

| Homocysteine (μM) amount added | Homocysteine (μM) (ELISA) | SEM | % Recovery |
|---|---|---|---|
| 5 | 2.9 | 1.0 | 58 |
| 25 | 23.8 | 5.6 | 95.2 |
| 50 | 40.7 | 7.4 | 81.4 |
| 75 | 78.3 | 12.2 | 104.4 |
| 100 | 123.6 | 14.1 | 123.6 |

3. Discussion

Physical Characterization of the Homocystamide Adduct—The Preparation of an Immunogen Capable of Generating Specific Antibodies Homocysteinemia is an emerging risk factor for the accelerated development of a number of medical conditions (2, 6–7, 17, 30, 33, 35, 47, 50, 52–53, 59, 62–67, 68–70, 72–76, 81–84, 96, 105, 107–111, 114–116, 118, 121). In recent years, the pathways of homocysteine metabolism have been elucidated (25–26). It has been demonstrated that a highly reactive thiolactone, homocysteine thiolactone, forms by an enzymatic mechanism in a number of cell lines including human cells (43–46). This thiolactone is highly reactive toward primary amines in biological conditions (45). Investigators have speculated that endogenous homocysteine thiolactone (formed enzymatically) could react with primary amines in viva (45, 59, 63–67, 72, 74–76, 115–116). The issue is unresolved, as physical technique has not been available in order to identify unequivocally the homocystamide adduct.

In FIG. 2, approximately 240 nmol thiol/mg LDL (corresponding to 120 nmol thiol groups per molecule of LDL) were bound to LDL at 75 minutes. Based on the levels of LDL-bound thiol groups generated in the reaction between N-acetyl-homocysteine thiolactone and LDL, we conclude that the ε-amino groups of apo-B lysyl residues had become 83% acylated after 3 hours (assuming 181 lysyl residues per apo-B molecule and a molecular weight of 500 kDa) (18). The rate of thiol group appearance (1.3 nmol/mg·min) in this reaction, however, is much slower than in the reaction between homocysteine thiolactone and LDL (5.9 nmol/mg·min) (FIG. 2). This suggests that the stoichiometry between apo-B lysyl residues and homocysteine thiolactone is not 1 to 1, as shown in equation 1 (FIG. 1). It has been speculated that homocysteine thiolactone may be capable of forming homocysteinyl-homocysteine thiolactone via intermolecular nucleophilic addition reactions and that this intermediate would be capable of additional acylation reactions, although this possibility has not been investigated experimentally (equation 5, FIG. 1) (76). We believe that this addition product could form under our experimental conditions. Subsequently, homocysteinyl-homocysteine thiolactone could react with LDL (equation 6, FIG. 1). This mechanism could explain the disparity in the rates of LDL-bound thiol group formation in the reactions between LDL and either homocysteine thiolactone or N-acetyl-homocysteine thiolactone (FIG. 2).

We have demonstrated that the reaction between homocysteine thiolactone and LDL results in an increase in LDL-bound thiol groups (21). These thiol groups are exposed to the aqueous phases of LDL, as demonstrated by the ESR spin-labeling experiments (FIG. 3) (21). Moreover, we have used LDL as a "model" carrier molecule to demonstrate the preparation of a compound capable of generating specific antibodies in animals. The techniques presented here could be used generating homocystamide adducts on any primary amine-containing compound. Thus, for the production of antibodies, one could generate homocystamide adducts of other carrier molecules including, but not limited to ovalbumin, KLH, thyroglobulin, and BSA, for example. These homocystamide adducts would be bound to these other compounds in the same manner, as we have demonstrated by monitoring thiol group content and ESR spin labeling. In conclusion, we have shown for the first time, a method for the preparation of a large carrier molecule bound to high quantities of homocystamide adducts (21, 23).

Immunogenicity of the Homocystamide Adduct and Antibody Specificity

As described in this report, we have raised polyclonal antiserum directed against the homocystamide adduct (23). We determined that the antiserum was directed against the homocystamide adduct, irrespective of the carrier molecule to which it is bound (23). In this report, we have also described the preparation of an μ-aminohexylsepharose-bound homocysteine antigen column, which we have used for the purification of this polyclonal antiserum. The protocol for antibody purification was described. In addition, the purified antibody was characterized. We found that the immunoglobulin class was mostly IgG, as demonstrated by the use of heavy chain-specific, heavy and light chain-specific, and μ-chain-specific secondary antibodies (FIG. 8). This is consistent with the timing of the immunization, as this antiserum was obtained following the fourth immunization. Competition ELISAs indicate that the purified polyclonal antibody is directed against the homocystamide adduct, regardless of the protein to which the adduct is bound. Neither non-specific lysine modifications (acetylated LDL) nor similar lysine modifications (N-acetyl homocystamide-LDL adduct, homoseramide-LDL adduct) were recognized. Homocystine competed for binding to the purified antibody, however, with much less affinity than protein-homocystamide adducts, as the binding curve was much more shallow and right-shifted.

The preparation of homocystamide-protein adduct involves the addition of homocysteine thiolactone free base directly to the protein in aqueous solution. Following an incubation period, protein is separated from the unreacted homocysteine thiolactone using a Sephadex G-25 column. In order to address the issue that the homocystamide adduct was indeed bound to the protein following this process, Western blots were performed. These data indicate that the homocystamide-protein adduct co-localizes with the protein. In addition, as these experiments were performed using denaturing conditions, these data show that the purified polyclonal antibody is directed against denatured homocystamide-protein adducts.

Figure 9:
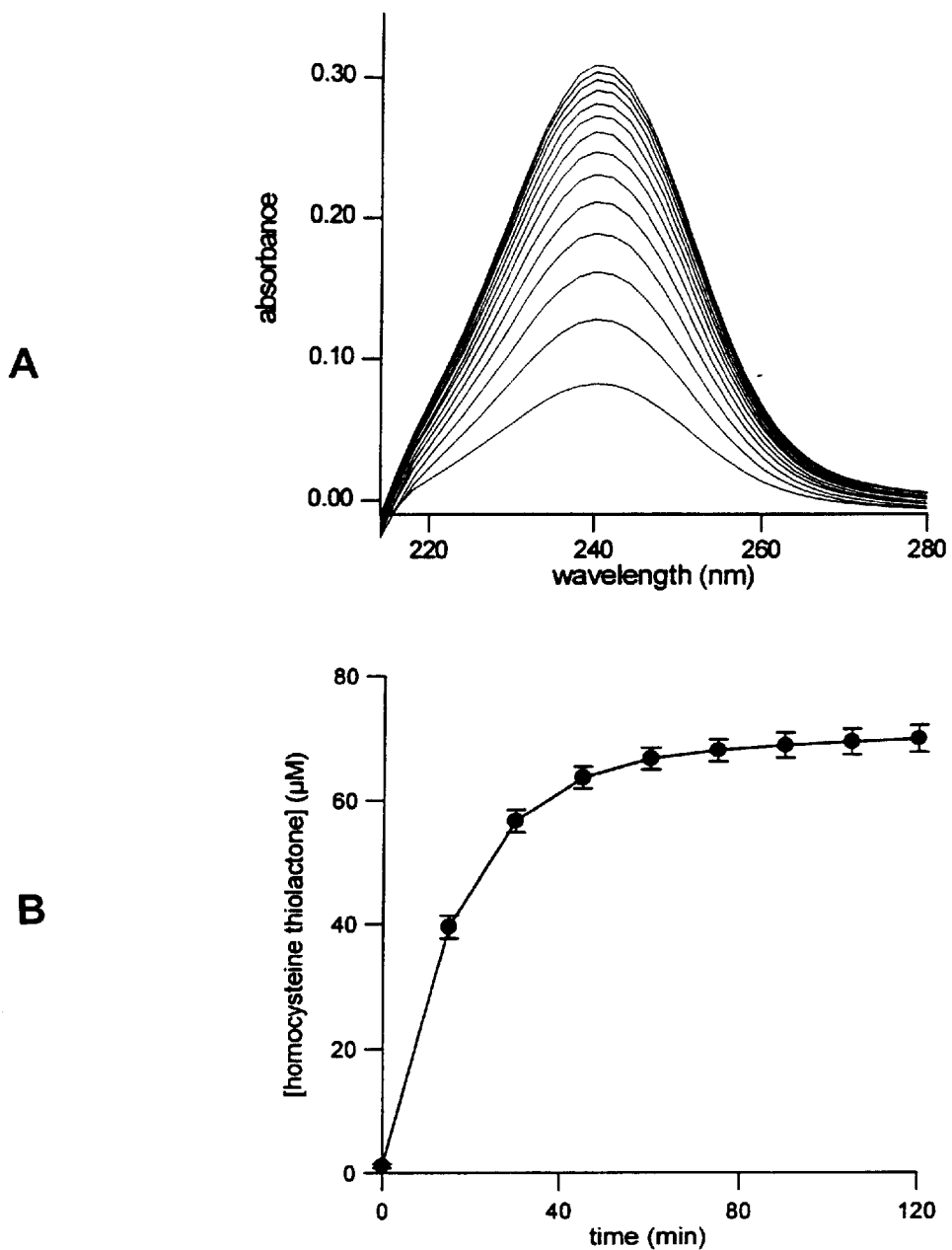
FIGS. 9A and B show temperature-dependent kinetics of homocysteine thiolactone formation from homocysteine in the presence of HCl.
FIG. 9B is as FIG. 9A, but the experiment was carried out for 2 hours at 60° C. Homocysteine concentrations (●) were calculated from a standard curve of authentic homocysteine thiolactone as described in Materials and Methods.

Utility of an antibody directed against homocysteine thiolactone-modified proteins. The development of an immunoassay for plasma homocysteine is an active area of research, as homocysteinemia is associated with a number of pathologies including vascular-occlusive disorders (2, 6–7, 17, 30, 33, 35, 47, 50, 52–53, 59, 62–67, 68–70, 72–76, 81–84, 96, 105, 107–111, 114–116, 118, 121). Here, the concepts for the development of an immunoassay for plasma homocysteine have been shown (FIG. 13). Each step the assay has been investigated. In FIG. 9, the conditions required for rapid thiolactone formation were determined. Table 1 shows that conversion of homocysteine to homocysteine thiolactone is essentially complete. We also established that plasma did not interfere with homocysteine thiolatone formation. Coupling of homocysteine to BSA was verified using ESR. It was demonstrated that our antibody was capable of recognizing converted homocystamide adducts in human plasma that contained known amounts of homocysteine. Lastly, it was determined that carrier molecules other than BSA could be used in order to accomplish this assay. L-lysine was shown to be an effective carrier molecule, as the antibody-binding profile was in the range of plasma homocysteine concentrations. We demonstrated that quantitative analysis of homocysteine in plasma is possible.

Figure 14:
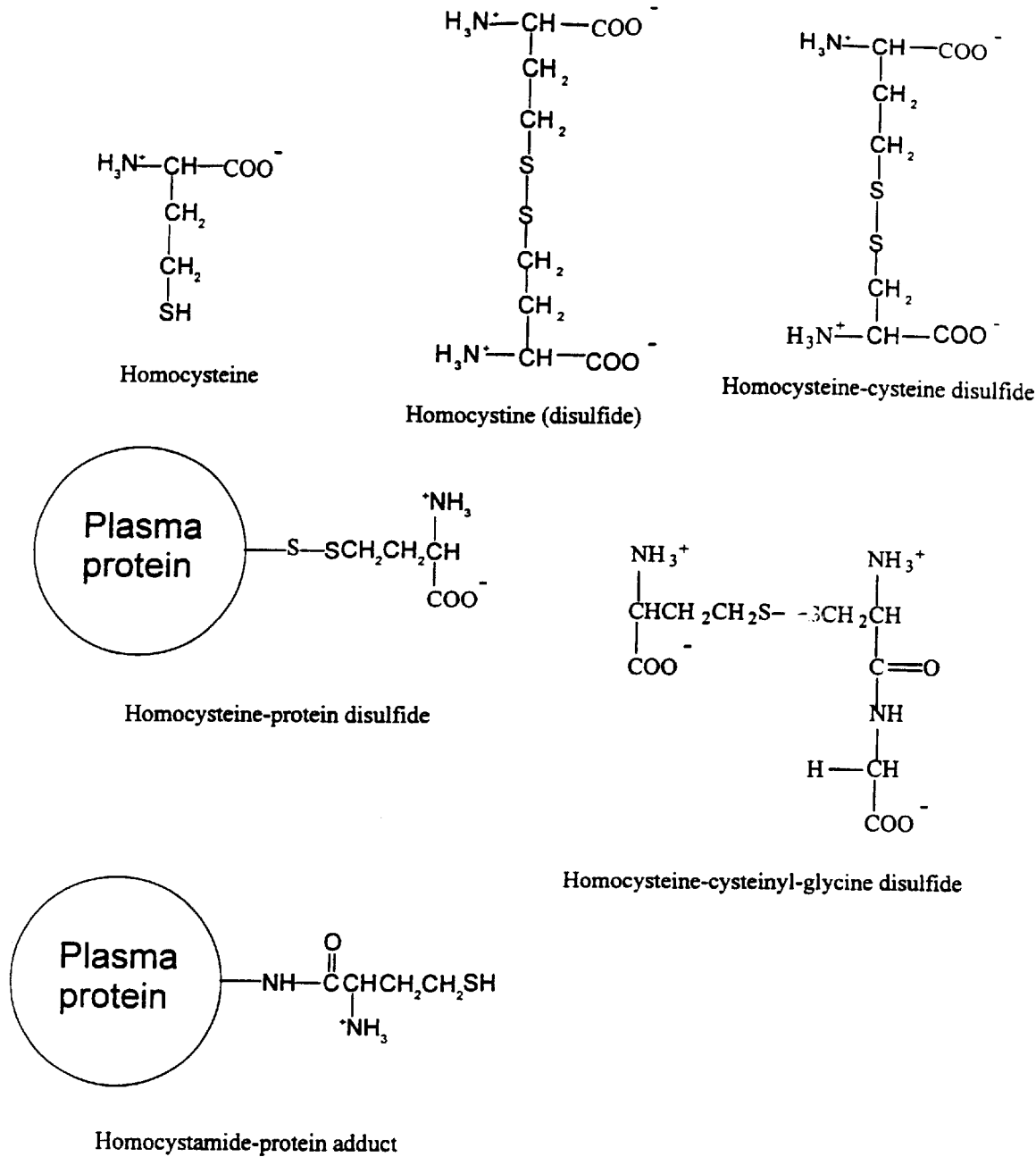
FIG. 14 describes forms of homocysteine in the plasma. Homocysteine can exist in the plasma as free homocysteine, homocysteine disulfide (homocystine), or as a mixed disulfide. The homocystamide adduct is thought to occur in homocysteinemia.

The sensitivity of the present assay is within the range of plasma homocysteine concentrations (FIG. 12, Tables 2–3). In these experiments, we have intentionally omitted reducing agents from the assays. This is for the purpose of obtaining plasma samples free of homocysteine that could be spiked with known values of reduced homocysteine. It is well known that homocysteine exists mainly as a disulfide in plasma, mostly protein-bound (107). There is a negligible portion of "free" homocysteine. In the present format, the removal of plasma proteins is essential due to the addition of HCl, which causes incomplete precipitation of plasma components. For the measurement of the total amount of endogenous plasma homocysteine, the format would be the same (FIGS. 11–12, Tables 2–3), however, a reduction step is required in order to free disulfide-bound homocysteine (e.g., homocystine, homocysteine-cysteine disulfide, homocysteine-cysteinylglycine, homocysteine-protein disulfide) (FIG. 14). (It remains unknown whether endogenous homocystamide adduct exists in plasma, as indicated in FIG. 14. Reduction would not release the homocystamide adduct, although it is possible to assay for this adduct directly). This reduction step is not unique to this assay, as it is employed in all assays that detect total plasma homocysteine (20, 24, 107). In addition, samples containing excess of 150 $\mu$M homocysteine would need to be diluted in order to be within the limits of the assay.

Comparison of the present immunoassay with other techniques. Measurement of plasma homocysteine is typically accomplished by HPLC (20, 24). This procedure yields accurate and precise results, but the analysis is inherently a low throughput procedure (~60–80 samples/day). This number includes the necessary standards (~10 samples). Therefore, if each plasma specimen is analyzed in triplicate, the throughput is only approximately 16–25 specimens per day. In addition, a highly skilled technician is required in order to keep an HPLC setup running. For these reasons, the present format may afford many advantages over HPLC, as the assay allows for simultaneous determination of homocysteine concentrations in many samples. This property could be useful in large scale clinical settings in which hundreds of specimens are processed. The present assay could handle hundreds of samples, in triplicate, in addition to the required standards in about 1 day. With the data obtained, one could stratify the population based on moderate (15–30 $\mu$M), intermediate (30–100 $\mu$M), and severe (>100 $\mu$M) homocysteinemia and match outcomes (e.g., myocardial infarction, plasma lipoprotein profile, thermolabile methyltransferase, etc.) to the groups. We conclude that this assay may be useful for the measurement of homocysteine in human plasma. This may prove to be a vast improvement over previous methods, as the simplicity of the method may allow for widespread use in epidemiological studies that could provide more important clues toward further elucidating the relationship between homocysteinemia and the associated medical conditions and disorders.

In addition, as it remains unknown whether homocystamide adducts exist in vivo (e.g., as a result of endogenous, enzymatically formed homocysteine thiolactone). We speculate that our antibodies could be used in order to probe for the presence and quantity of homocystamide adducts in biological tissue (e.g., plasma, brain, liver, heart, kidney, blood vessels, etc.).

4. References

1. Benesch R, Benesch R E. 1956 Formation of peptide bonds by aminolysis of homocysteine thiolactone. *J. Amer. Chem. Soc.* 78, 1597–1599.
2. Berg M V D, Stenhouwer C D A, Bierdragen E, Rauwerda J A. 1996 Plasma homocysteine and severity of atherosclerosis in young patients with lower-limb atherosclerotic disease. *Arterioscl. Thronib. Vasc. Biol.* 16, 165–71.
3. Berliner U, Grunwald J, Hankovsky H O, Hideg K. 1982 A novel reversible thiol-specific spin label: papain active site labeling and inhibition. *Anal. Biochem.* 119, 450–455.
4. Blom H J. 1998 Mutated 5,10-methylenetetrahydrafolate reductase and moderate hyperhomocysteinaemia. *Eur. J. Pediatr.* 157, S131–S134.
5. Blundell G, Jones B G. Rose F A, Tudball N 1996 Homocysteine mediated endothelial cell toxicity and its amelioration. *Atherosclerosis* 122, 163–172.
6. Doers G. 1998 Moderate hyperhomocysteinaemia and vascular disease: evidence, relevance and the effect of treatment. *Eur. J. Pediatr.* 157, S127–130.
7. Boushey C J, Beresford S A A, Omenn G S, et al. 1995 A quantitative assesment of plasma homocysteine as a risk factor for vascular disease: probable benefits of increasing folic acid intakes. *JAMA* 274, 1049–1057.
8. Boyd H, Gown A, Wolfbauer G, Chait A. 1989 Direct evidence for a protein recognized by a monoclonal antibody against oxidatively modified LDL in atherosclerotic lesions from a Watanabe heritable hyperlipidemic rabbit. *Am. J. Pathol.* 135, 815–825.
9. Carson N A J, Dent C E, Field C M B, Gaull G E. 1965 Homocysteinuria. Clinical and pathological review of 10 cases. *J. Pediatrics* 66, 565–583.
10. crowther J R: ELISA: theory and practice. 1995; Humana Press Inc., Totowa, N.J.
11. Csukas S, Hanke C J, Rewolinski D, Campbell W B. 1998 Prostaglandin $E_2$-indueed aldosterone release is mediated by an $EP_2$ receptor. *Hypertension* 31, 575–581.

12. deweck, A L. 1963 Newer developments in penicillin immunochemistry. *Int. Arch. Allergy Appl. Immunol.* 22, 245–252.
13. Du Vigneaud V, Patterson W I, Hunt M. 1938 Opening the ring of the thiolactone of homocysteine. *J. Biol. Chem.* 126, 217–231.
14. Duddman N P B, Wilken D E L. 1981 Homocysteine thiolactone and experimental homocyst(e)inemia. *Biochem. Med.* 27, 244–53.
15. Duddman N P B, Wilken D E L. 1991 Homocysteine thiolactone disposal by human arterial endothelial cells and serum in vitro. *Arterioscler. Thromb.* 11, 663–670.
16. Duerre J A, Miller C H. 1966 Preparation of L-homocysteine from L-homocysteine thiolactone. *Analytical Biochem.* 117, 310–315.
17. Eskes TKAB. 1998 Neural tube defects, vitamins and homocysteine. *Eur. J. Pediatr.* 157, S139–S141.
18. Esterbauer H, Gebicki H, Puhl H, Jurgens G. 1990 The role of lipid peroxidation and antioxidants in oxidative modification of LDL. *Free Rad. Biol. Med.* 13, 341–390.
19. Esterbauer H, Striegl G, Puhl H, Rotheneder M. 1989 Continuous monitoring of in vitro oxidation of human low density lipoprotein. *Free Rad. Res. Commun.* 6, 67–75.
20. Fahey R C, Newton G L. 1987 Determination of low-molecular-weight thiols using monobromobimane fluorescent labeling and high performance liquid chromatography. *Met. Enzymol.* 143, 85–96.
21. Ferguson E, Hogg N, Antholine W E, Joseph J, Singh R J, Parthasarathy S, Kalyanaraman B. 1998 Characterization of the adduct formed in the reaction between homocysteine thiolactcne and low density lipcprotein: antioxidant implications. *Free Radic. Biol. Med.* (in press).
22. Ferguson E, Sinqh R J, Hogg N, and Kalyanaraman B. 1997 The mechanism of apolipoprotein B-100 thiol depletion during oxidative modification of LDL. *Archives Biochem. Biophys.* 341: 287–294.
23. Ferguson E, Parthasarathy S, Joseph J, Kalyanaraman B. 1998 Generation and initial characterization of a novel polyclonal antibody directed against homocysteine thiolact.one-modified low density lipoprotein. *J. Lipid Res.* 39, 925–933.
24. Feussner A, Rolinski B, Weiss N, Deufel T, Wolfram G, Roscher A A. 1997 Determination of total homocysteine in human plasma by isocratic high performance liquid chromatography. *Eur. J. Clin. Chem.* 35, 687–691.
25. Firikelstein. 1998 The metabolism of homocystiene: pathways and regulation. *Eur. J. Pediatr.* 157, S40–44.
26. Fowler B. 1998 Genetic defects of folate and cobalamin metabolism. *Eur. J. Pediatr.* 157, S60–66.
27. Franten F, Faaren A L, Alfheim I, Nordhei A K. 1998 Enzyme conversion immunoassay for determining total homocysteine in plasma or serum. *Clin. Chem.* 44, 311–316.
28. Frauscher G, Karnauhnova E, Muehl A, Hoeger H, Lubec B. 1995 Oral administration of homocysteine leads to increased plasma triglycerides and homocysteic acid— additional mechanisms in homocysteine induced endothelial damage? *Life Sciences* 57, 813–17.
29. Gorqel D, Cederbaum A. 1997 Interaction of nitric oxide with 2-thio-5-nitrobenzoic acid: implications for the determination of free sulfhydryl groups by Ellman's reagent. *Arch. Biochem. Biophys.* 342, 282–288.
30. Gupta A, Robinson K. 1997 Hyperhomocysteinaemia and end stage renal disease: *J. of Nephrology* 10, 77–84.
31. Haberland M, Fong B, Cheng U. 1988 Malondialdehyde-altered protein occurs in atheroma of Watzanabe heritable hyperlipidemic rabbit. *Science* 241, 215–218.
32. Halvorsen B, Brude I, Drevon C A, Nysom J, Ose U, Christiansen E N, Nenseter M S. 1996. Effect of homocysteine on Copper-ion-catalyzed, azo compound-initiated, and mononuclear cell-mediated oxidative modifications of low density lipoprotein. *J. Lipid Res.* 37, 1591–1600.
33. Harker L A, Ross R, Slichter S J, Scott C R. 1976 Homocystine-induced arteriosclerosis *J. Clin. Invest.* 58, 731–741.
34. Harlow E, Lane D: Antibodies, a laboratory manual. 1988; Cold Spring Harbor Laboratory, Cold Spring Harbor, N.Y.
35. Harpel P C. 1997 Homocysteine, atherogenesis and therombosis. *Fibrinolysis and Proteolysis* 11, 77–80.
36. Hatch F T, Lees R S. 1968 Practical methods for plasma lipoprotein analysis. *Adv. LipidRes.* 6, 2–68.
37. Heinecke J W, Kawamura M, Suzuki U, Chait A. 1993 Oxidation of low density lipoprotein by thiols: superoxide-dependent and -independent mechanisms. *J. Lipid Res.* 34:2051–2061.
38. Heinecke J W, Rosen H, Suzuki L A, Chait A. 1987 The role of sulfur-containing amino acids in superoxide production and modification of low density lipoprotein by arterial smooth muscle cells. *J. Biol. Chem.* 262:10098–10103.
39. Hirario K, Ogihara T, Miki M, Yasuda H, Tamai H, Kawamura H, and Mino M. 1994 Homocysteine induces iron-catalyzed lipid peroxidation of low-density lipoprotein that is inhibited by alpha-tocopherol. *Free Rdd. Res.* 21: 267–76.
40. Hogg N, Darley-Usmar V, Wilson M T, Moncada S. 1993 The oxidation of (-tocophorol in human low-density lipoprotein by the simultaneous generation of superoxide and nitric oxide. *FEBS Lett.* 326, 199–203.
41. Hogg N, Joseph J, Kalyanaraman B. 1994 The oxidation of (-tocopherol and trolox by peroxynitrite. *Arch. Biochem. Biophys.* 314, 153–158.
42. Izui S. 1994 Autoimmune hemolytic anemia. *Curr. Opin. Immunol.* 6, 926–930.
43. Jakubowski H, Goldman E. 1993 Synthesis of homocysteine thiolactone by methionyl-tRNA synthetase in cultured mammalian cells. *FEBS Lett.* 317, 237–40.
44. Jakubowski H. 1994 Energy cost of translocation proofreading in vivo. The aminoacylation of transfer RNA in *E. Coli. Ann. N.Y. Acad. Sci.* 745, 4–20.
45. Jakubowski H. 1997 Metabolism of homocysteine thiolactone in human cell cultures. *J. Biol. Chem.* 272, 1935–42.
46. Jakubowski, H. 1996 Proofreading in vivo: editing of homocysteine by aminoacyl-tRNA synthetases in *Escherechia Coli. J. Bid. Chem.* 270, 17672–17673.
47. Jensen M K, Ekeland S, Svendsen U. 1996 Folate and homocysteine satus and haemolysis in patients treated with sulphasalazine for arthritis. *Scand. J. Clin. Lab. Invest.* 56: 421–9.
48. Jurgens G, Ashy A, Esterbauer H. 1990 Detection of new epitopes formed upon oxidation of low-density lipoprotein. Use of an antiserum against 5-hydroxynoneal-modified low-density lipoprotein. *Biochem. J.* 265, 605–608.
49. Kane J P, Malloy M J, Ports T A, Phillips N R, Diehl J C, Havel R J. 1990 Regression of coronary atherosclerosis during treatment of familial hypercholesterolemia with combined drug regimens. *J.A.M.A.* 264: 3007–3012.
50. Kang 55, Wong P W, Malinow M R. 1992 Hyperhomocysteinemia as a risk factor for vascular occlusive disease. *Ann. Rev. Nutr.* 12, 279–298.

51. Kannel W E 1988 Contributions of the Framingham study to the conquest of coranary artery disease. *Amer. J. Cardiol.* 62, 1109–1112.
52. Koch H G, Goebeler M, Marquardt T, Roth J, Harms E. 1998 The redox status of aminothiols as a clue to homocyteine-induced vascular damage? *Eur. J. Pediatr.* 157, S102–S106.
53. Konecky N K, Malinow M R, Tunick P A, Freedberg R S, Rosenzweig B P, Katz E S Hess D L, Upson B, Leung B, Perez J, Kronzon I. 1997 Correlation between plasma homocyst(e)ine and aortic atherosclerosis. *Amer. Ht. J.* 133: 534–40.
54. Laemmli U K. 1970 Cleavage of structural proteins during the assembly of the head of bacteriophage T4. *Nature* 227, 680–5.
55. Lafaye P, Lapresele C. 1988 Fixation of penicilloyl groups to albumin and the appearance of anti-penicilloy antibodies in penicillin-treated patients. *J. Clin. Invest.* 82, 7–12.
56. Levine B B, Ovary Z. 1961 Studies on the mechanism of the formation of the penicillin antigen III. The N-(D-(-benzylpenicilloyl) group as an antigenic determinent responsible to hypersensitivity to penicillin G. *J. Exp.Med.* 114, 875–904.
57. Lim Y S, Cha M K, Kim H K, Uhm T B, Park J W, Kim K, Kim I H. 1993. Removals of hydrogen peroxide and hydroxyl radical by thiol-specific antioxidant protein as a possible role in vivo. *Biochem. Biophys. Res. Commun.* 192, 273–80.
58. Lipid Research Clinics Program: the lipid research clinics coronary primary prevention trial results I. Reduction in incidence of coronary artery disease. 1984 *J.A.M.A.* 251, 351–364.
59. Loscalzo J. 1996 The oxidant stress of hyperhomocyst(e)inemia. *J. Clin. Invest.* 98, 5–7.
60. Lowry O H, Rosenbrough N J, Farr, A U, Randall R J. 1951 Protein measurement with the Folin phenol reagent. *J. Biol. Chem.* 193, 265–275.
61. Lynch, S M, Frei B. 1997 Physiological thiol compounds exert pro- and anti-oxidant effects, respectively, on iron- and copper-dependent oxidation of human low-density lipoprotein. *Biochim. Biophys. Acta* 1345, 215–221.
62. Manilow M R, Sexton G, Averbuch M, Grossman M, Wilson D, and Upsori B. 1990 Homocyst(e)inemia in daily practice: levels in coronary artery disease. *Coronary Artery Disease* 1, 215–220.
63. McCully K S, and Vezeridis M P. 1989 Histopathological effects of homocysteine thiolactone on epithelial and stromal tissues. *Exper. Molec. Pathol.* 51, 159–170.
64. McCully K S, Vezeridis M P. 1988 Homocysteine thiolactone in atherosclerosis and cancer. *Res. Comm. Chem. Pathol. Pharmacol.* 59, 107–119.
65. McCully K S, Vezeridis M P. 1987 Chemopreventitive and antineoplastic activity of N-acety homocysteine thiolactonyl retinamide. *Carcinogenesis* 8, 1559–62.
66. McCully K S. 1996 Homocysteine and vascular disease. *Nature Med.* 2, 386–89.
67. McCully K S. 1993 Chemical pathology of homocysteine I. Atherogenesis. *Ann. Clin. Lab. Med.* 23, 477–493.
68. Miller J W, Nadeati M R, Smith B, Selhub J. 1994 Vitamin B-6 deficiency vs. folate deficiency: comparison of responses to methionine loading in rats. *Amer. J. Clin. Nutr.* 59, 1033–1039.
69. Miner S E S, Evrovskii J, Cole DEC. 1997 Clinical chemistry and molecular biology of homocysteine metabolism-an update. *Clin. Biochem.* 30, 189–201.
70. Mudd S H, Levy H L, Skovby F. 1995 Disorders of transsulfuration. In: The metabolic and molecular bases of inherited disease. (eds. Scriver C R, Beaudet A L, Sly W S, Valle B) McGraw-Hill, New York, pp. 1279–1327.
71. Narparstek Y, Plotz P H. 1993 The role of autoantibodies in autoimmune disease. *Annu. Rev. Immunol.* 11, 79–104.
72. Naruszewicz M, Mirkiewicz E, Olszewski A J, McCully K S. 1994 Thiolation of low-density lipoprotein by homocysteine thiolactone causes increased aggregation and altered interaction with cultured macrophages. *Nutrit. Metab. Cardicvasc. Dis.* 4, 70–77.
73. Neugebauer S, Tsunehara B, Kurokawa K, Watanabe T. 1997 Defective homocysteine metabolism as a risk factor for diabetic retinopathy. *The Lancet* 349, 473–4.
74. Olszewski A J, McCully K S. 1991 Homocysteine content of lipoproteins in hyercholesterolemia. *Atherosclerosis* 88, 61–68.
75. Olszewski A J, Szostak W B. 1988 Homocysteine content of plasma lipoproteins in ischemic heart disease. *Atherosclerosis* 69, 109–13.
76. Olzewski A J, McCully K S. 1993 Homocysteine metabolism and the oxidative modification of proteins and lipids. *Free Rad. Biol. Med.*14, 683–93.
77. Palinski W, Rosenfeld M, Yla-Herttualla S. Gurtner G, Socher S, Butler S, Parthasarathy S, Carew I, Steinberg D, and Witztum J: Low density lipoprotein undergoes oxidative modification in vivo. 1989 *Proc. Natl. Acad. Sci. USA* 86, 1372–1376.
78. Parker C W, Shapiro J, Kern M, Eisen, H N. 1962 Hypersensitivity to penicillic acid derivatives in human beings with penicillin allergy. *J. Exp. Med.* 115 821–838.
79. Parthasarathy S. 1987 Oxidation of low-density lipoprotein by thiol compounds leads to its recognition by the acetyl UDL receptor. *Biochim. Biophys. Acta* 917, 337–340.
80. Parthasarathy, S. (1994) Modified Lipoproteins in the Pathogenesis of Atherosclerosis. R G Landes Company. Austin, Tex.
81. Petri M, Rowbenoff R, Dallal G E, Nadeau M R, Selhub J, Rosenberg I H. 1996 Plasma homocysteine as a risk factor for antithrombotic events in systemic lupus erythematosus. *The Lancet* 348, 1120–24.
82. Pettersson T, Friman C, Abrahamsson U, Nilsson B, Norberg B. 1998 Serum homocysteine and methylmalonic acid in patients with rheumatoid arthritis and cobalaminopenia. *J. Rheumatol.* 25, 859–863.
83. Pietrzik K, Bronstrup A. 1998 Vitamins $B_{12}$, $B_6$ and folate as determinants of homocysteine concentration in the healthy population. *Eur. J. Pediatr.* 157, S135–138.
84. Refsum H, Ueland P M, Nygard O, Vcllset S E. 1998 Homocysteine and cardiovascular disease.*Ann. Rev. Med.* 49, 31–62.
85. Riddles P W, Blakely R L, Zerner B: Ellman's Reagent: 5,5,dithiobis (2-nitrobenzoic acid)-a reexamination. 1979 *Anal. Biochem.* 9, 75–81.
86. Rosenquist T H, Ratashak S A, Selhub J. 1996 Homocysteine induces defects of the heart and neural tube: effect of folic acid. *Proc. Natl. Acad. Sci. USA* 93, 15227–32.
87. Santanam N, Parthasarathy S. 1995 Cellular cysteine does not contribute to the initiation of LDL oxidation. *J. Lipid Res.* 36, 2203–2211.
88. Santanam N, Parthasarathy S. 1995 Paradoxical actions of antioxidants in the oxidation of low density lipoprotein. *J. Clin. Invest.* 95, 2594–2600.
89. Schimke R N, McKusick V A, Huang T, Pollack A D. 1965 Homocysteinuria. Studies of 20 families with 38 affected members. *JAMA* 193, 711–719.
90. Sevilla M D, Becker B, Yan M. 1990 The formation and structure of the sulfoxyl radicals RSO., RSOO., RSO.$_2$, 90. ...and RSO$_2$OO. from the reaction of cysteine, glutathione and penicillamine thiyl radicals with moecular oxygen. *Int. J. Rad. Biol.* 57, 65–81.
91. Shipchandler M T, Moore E G. 1995 Rapid, fully automated measurement of plasma homocyst(e)ine with the Abbott IMx® Analyzer. *Clin. Chem.* 41, 991–994.
92. Singh R, Feix J, Mchaourab H, Hogg N, Kalyanaraman B. 1995 Spin-labeling study of oxidative damage to low-density lipoprotein. *Arch. Biochem. Biophys.* 320, 155–161.
93. Sparrow C P, Olszewski J. 1993 Cellular oxidation of low density lipoprotein is caused by thiol production in media containing transition metal ions. *J. Lipid Res.* 34:1219–1228.
94. Spindel E, and McCully K S. 1974 Conversion of methionine to homocysteine thiolactone in liver. *Biochim. Biophys. Acta* 343, 687–91.
95. Starkebaum G, Harlan J M. 1986 Endcthelial cell injury due to copper-catalyzed hydrogen peroxide generation from homocysteine. *J. Clin. Invest.* 77, 1370–76.
96. Stehouwer C D A, Jakobs C. 1998 Abnormalities of vascular function in hyperhomocysteinaemia: relationship to atherothrombotic disease. *Eur. J. Pediatr.* 157, S107–S111.
97. Steinberg B, Parthasarathy S, Carew T, Khoo J, and Witztum J. 1989 Beyond cholesterol: oxidative modifications of low density lipoprotein that increase its atherogenicity. *New England J. Med.* 320, 915–924.
98. Steinberg B. 1997 Low density lipoprotein and its pathobiological significance. *J. Biol. Chem.* 272, 20963–6.
99. Steinbrecher U P, Fisher M, Witztum J L, Curtiss U K. 1984 Immunogenicity of homologous low density lipoprotein after methylation, ethylation, acetylation, or carbamylation: generation of antibodies specific for derivatized lysine. *J. Lipid Res.* 25, 1109–16.
100. Steinbrecher U P, Witztum J L, Parthasarathy S, Steinberg D. 1987. Decrease in reactive amino groups during oxidation or endothelial cell modification of LDL. Correlation with changes in receptor-mediated catabolism. *Arteriosclerosis* 7, 135–143.
101. Steinbrecher U P, Zhang H, Lougheed M. 1990 Role of oxidatively modified LDL in atherosclerosis. *Free Rad. Biol. Med.* 9, 155–168.
102. Sturgess A. 1992 Recently characterised auto antibodies and their clinical significance. *Aust. N. Z. J. Med.* 22, 279–289.
103. Superko H R. 1995 New aspects of risk factors for the development of atherosclerosis including small low-density lipoprotein, homocyst (e) me, and lipoprotein(a). *Curr. Cpin. Cardiol.* 10, 347–354.
104. Swain J A, Darley-Usmar V, Gutteridge J M C. 1994 Peroxynitrite releases copper from caeruloplasmin: implications for atherosclerosis. *FEBS Lett.* 342, 49–52.
105. Swain R, StClair L. 1997 The role of folic acid in deficiency states and prevention of disease. *J. Family Prac.* 44, 138–44.
106. Tobwin H, Staehelin T, Gordon J. 1979 Electrophoretic transfer of proteins from polyacrylamide gels to nitrocellulose sheets: procedures and applications. *Proc. Natl. Acad. Sci. USA* 76, 4350–4.
107. Ueland P M. 1995 Homocysteine species as components of plasma thiol redox status. *Clin Chem.* 41, 340–342.
108. Ueland P M, Refsum H, Battstrom L. 1992 Plasma homocysteine and cardiovascular disease. In Atherosclerotic cardiovascular disease, hemostasis and endcthelial function. ed. Francis R B Jr. pp. 183–266. New York: Dekker.
109. Ueland P, Refsum H. 1989. Plasma homocysteine, a risk factor for vascular disease: plasma levels in health, disease, and drug therapy. *J. Lab. Clin. Med.* 51, 159–170.
110. Ueland P M, Ref sum H, Stabler S P, Malinow M R, Andersson A, Allen R H. 1993 Total hamocysteine in plasma or serum: methods and clinical applications. *Clin. Chem.* 39, 1764–79.
111. Verhoef P, Kok F J, Kruyssen D A C M, Scouten E G, Witteman J C M, Grobbee B E, Ueland P M, Refsum H. 1997 Plasma homocysteine, B vitamins and risk of coronary atherosclerosis. *Arterioscl. Thromb. Vasc. Biol.* 17, 989–995.
112. Vidal M, Sainte-Marie J, Philippot J, Bienvenue A. 1986 Thiolation of low-density lipoproteins and their interaction with L$_2$C leukemic lymphocytes. *Biochimie* 68, 723–730.
113. Vigo P, Mayer E L, Selhub J, Kuther N, Jacobsen, D W. 1997 Hyperhcmocysteinemia confers an independent increased risk of atherosclerosis in end-stage renal disease and is closely linked to plasma folate and pyridoxine concentrations: *Circulation* 94, 2743–48.
114. Wall R T, Harlan J M, Harker L A, Striker G E. 1980 Homocysteine-induced endothelial cell injury in vitro: a model for the study of vascular injury. *Thrombosis Research* 18, 113–121.
115. Welch G N, Uoscalzo J. 1998 *New Engl. J. Med* 338, 1042–50.
116. Welch, G N, Upchurch, J R, Loscalzo, J. 1997 Homocysteine, oxidative stress, and vascular disease. *Hospital Practice* 32, 81–2.
117. White F Jr. 1970 Thiolation. *Meth. Enzymol.* 46, 541–46.
118. Wilken D E L. 1998 Homocysteine and vascular disease: *Med. J. Austrailia;* 168, 431–432.
119. Winterbourn C C. 1993 Superoxide as an intracellular radical sink. *Free Rad. Biol. Med.* 14:85–90.
120. Yla-Herttuala S, Palinski W, Rosenfeld N, Parthasarathy S, Carew T, Butler S, Witztum J, and Steinberg B. 1989 Evidence for the presence of oxidatively modified low density lipoprotein in atherosclerotic lesions in rabbits and man. *J. Clin. Invest.* 84, 1086–1095.
121. Young, P B, Kennedy, S, Molloy, A M, Scott, J M, Weir, D G, Kennedy, D G. 1997 Lipid peroxidation induced in vivo by hyperhomocysteinaemia in pigs. *Atheroscl.* 129, 67–71.

We claim:

1. A method of measuring total homocysteine levels, wherein total homocysteine levels comprise both reducible and non-reducible homocysteine, in a sample comprising the steps of:

(a) obtaining a sample, (b) treating the sample such that endogenous homocysteine is converted to a homocystamide adduct of a carrier molecule, wherein the adduct comprises homocysteine bound to another molecule by an amide bond, (c) exposing the sample to an antibody or a portion thereby which specifically forms a complex with a homocystamide adduct, wherein the antibody binding is specific to the homocysteine-amide bond, and wherein bound antibody is separated from unbound antibody; and (d) correlating the binding of the antibody to a standardized antibody binding profile in order to determine the total amount of homocysteine in the sample.

2. The method of claim 1 wherein the carrier molecule of step (b) is endogenous.

3. The method of claim 1 wherein the carrier molecule of step (b) is lysine.

4. The method of claim 1 wherein the conversion is via a reducing agent.

5. The method of claim 1 wherein the reducing agent is selected from the group consisting of dithiothreitol or tributylphosphine.

6. The method of claim 1 wherein the sample is a biological sample.

7. The method of claim 6 wherein the biological sample is human plasma.

* * * * *

UNITED STATES PATENT AND TRADEMARK OFFICE
CERTIFICATE OF CORRECTION

PATENT NO.     : 6,589,751 B2
DATED          : July 8, 2003
INVENTOR(S)    : Eric Ferguson et al.

It is certified that error appears in the above-identified patent and that said Letters Patent is hereby corrected as shown below:

Column 5,
Line 8, "AM)" should read -- uM --.

Column 26,
Line 63, "Crowther" should be capitalized -- Crowther --.

Column 27,
Line 1, "deweck" should read -- deWeck --.
Line 29, "thiolactcne" should read -- thiolactone --.
Line 39, "thiolac.one-" should read -- thiolactone- --.

Column 31,
Line 48, "homocyst(e)me," should read -- homocyst(e)ine, --.
Line 65, "endcthelial" should read -- endothelial --.

Column 32,
Line 5, "hamocysteine" should read -- homocysteine --.
Line 20, "Hyperhemocysteinemia" should be capitalized -- Hyperhomocysteinemia --.

Column 34,
Line 1, "of claim 1" should read -- of claim 4 --.

Signed and Sealed this

Tenth Day of February, 2004

JON W. DUDAS
*Acting Director of the United States Patent and Trademark Office*